US012360113B2

(12) United States Patent
Poynard

(10) Patent No.: US 12,360,113 B2
(45) Date of Patent: Jul. 15, 2025

(54) METHOD OF PROGNOSIS AND FOLLOW UP OF PRIMARY LIVER CANCER

(71) Applicants: BIOPREDICTIVE, Paris (FR); ASSISTANCE PUBLIQUE-HOPITAUX DE PARIS, Paris (FR)

(72) Inventor: Thierry Poynard, Paris (FR)

(73) Assignees: BIOPREDICTIVE, Paris (FR); ASSISTANCE PUBLIQUE-HOPITAUX DE PARIS, Paris (FR)

( * ) Notice: Subject to any disclaimer, the term of this patent is extended or adjusted under 35 U.S.C. 154(b) by 1500 days.

(21) Appl. No.: 16/754,164

(22) PCT Filed: Oct. 15, 2018

(86) PCT No.: PCT/EP2018/078108
§ 371 (c)(1),
(2) Date: Apr. 7, 2020

(87) PCT Pub. No.: WO2019/076830
PCT Pub. Date: Apr. 25, 2019

(65) Prior Publication Data
US 2021/0208147 A1 Jul. 8, 2021

(30) Foreign Application Priority Data

Oct. 16, 2017 (EP) ..................... 17306403
Jul. 27, 2018 (EP) ..................... 18306025

(51) Int. Cl.
| | |
|---|---|
| *G01N 33/574* | (2006.01) |
| *A61K 45/06* | (2006.01) |
| *G06F 17/18* | (2006.01) |
| *G16B 40/20* | (2019.01) |
| *G16H 20/00* | (2018.01) |
| *G16H 50/30* | (2018.01) |

(52) U.S. Cl.
CPC ....... *G01N 33/57438* (2013.01); *A61K 45/06* (2013.01); *G06F 17/18* (2013.01); *G16B 40/20* (2019.02); *G16H 20/00* (2018.01); *G16H 50/30* (2018.01); *G01N 2333/775* (2013.01); *G01N 2333/9108* (2013.01)

(58) Field of Classification Search
CPC ....... G01N 33/57438; G01N 2333/775; G01N 2333/9108; G01N 2333/81; G01N 2800/50; A61K 45/06; G06F 17/18; G16B 40/20; G16H 20/00; G16H 50/30; G16H 10/40
See application file for complete search history.

(56) References Cited

U.S. PATENT DOCUMENTS

2004/0039553 A1* 2/2004 Poynard ............. G01N 33/6893
702/190
2017/0032099 A1 2/2017 Cales et al.

FOREIGN PATENT DOCUMENTS

EP 2600266 A1 6/2013
EP 2799876 A2 11/2014

OTHER PUBLICATIONS

Marrero JA, Feng Z, Wang Y, et al. Alpha-fetoprotein, des-gamma carboxyprothrombin, and lectin-bound alpha-fetoprotein in early hepatocellular carcinoma. Gastroenterology. 2009;137(1):110-118. doi:10.1053/j.gastro.2009.04.005 (Year: 2009).*
Lin S, Hoffmann K, Schemmer P. Treatment of hepatocellular carcinoma: a systematic review. Liver Cancer. 2012;1(3-4):144-158. doi:10.1159/000343828 (Year: 2012).*
Lin, D.-Y., Lin, S.-M. and Liaw, Y.-F. (1997), Non-surgical treatment of hepatocellular carcinoma. Journal of Gastroenterology and Hepatology, 12: S319-S328. https://doi.org/10.1111/j.1440-1746.1997.tb00516.x (Year: 1997).*
International Search Report and Written Opinion issued on Jan. 11, 2019 for corresponding PCT Application No. PCT/EP2018/078108.
Mei-Hsuan Lee et al: "Prediction models of long-term Cirrhosis and hepatocellular carcinoma risk in chronic hepatitis B patients: Risk scores integrating host and virus profiles: Hepatology", Hepatology, vol. 58, No. 2, 2013, pp. 546-554 XP055442303.
Chi-Pang Wen et al: "Hepatocellular Carcinoma Risk Prediction Model for the General Population: The Predictive Power of Transaminases", Journal of the National Cancer Institute, vol. 104, No. 20, 2012, pp. 1599-1611 XP055442306.
Multivirc Group Imbert-Bismut et al: "Biochemical markers of liver fibrosis in patients with hepatitis C virus infection: a prospective study", The LA, The Lancet Publishing Group, GB, vol. 357, No. 9262, 2001, pp. 1069-1075 XP005061312.
Eldad S. Bialecki et al: "Diagnosis of hepatocellular carcinoma", HPB, vol. 7, No. 1, 2005, pp. 26-34 XP055535898.
Kristina Tzartzeva et al: "Surveillance Imaging and Alpha Fetoprotein for Early Detection of Hepatocellular Carcinoma in Patients With Cirrhosis: A Meta-analysis", Gastroenterology, vol. 154, No. 6, 2018, pp. 1706-1718 XP055535900.
Tara Behne et al: "Biomarkers for Hepatocellular Carcinoma", International Journal of Hepatology, vol. 2012, pp. 1-7 Article ID 859076.
Abdulaziz A. M. Alsalloom: "An update of biochemical markers of hepatocellular carcinoma", International Journal of Health Sciences, vol. 10, No. 1, 2016, pp. 121-136.
Hidenori Toyoda et al: "Tumor Markers for Hepatocellular Carcinoma: Simple and Significant Predictors of Outcome in Patients with HCC", Liver Cancer, vol. 4, 2015, pp. 126-136.
Yan-Jie Zhao et al: "Tumor markers for hepatocellular carcinoma (Review)", Molecular and Clinical Oncology, vol. 1, 2013, pp. 593-598.

* cited by examiner

*Primary Examiner* — Karlheinz R. Skowronek
*Assistant Examiner* — Nidhi Dharithreesan
(74) *Attorney, Agent, or Firm* — POLSINELLI PC

(57) ABSTRACT

The present invention relates to new methods for assessing the risk of a patient, in particular with chronic liver disease, to develop primary liver cancer over time, using functions combining blood biochemical markers.

5 Claims, 8 Drawing Sheets

METHOD OF PROGNOSIS AND FOLLOW UP OF PRIMARY LIVER CANCER

CROSS-REFERENCE TO RELATED APPLICATIONS

This application is a national stage application (under 35 U.S.C. § 371) of PCT/EP2018/078108, filed Oct. 15, 2018, which claims benefit of European Application No. 17306403.1, filed Oct. 16, 2017, and European Application No. 18306025.0, filed Jul. 27, 2018, which are incorporated herein by reference in their entireties.

The invention relates to a new non-invasive quantitative test that, in particular, makes it possible to detect patients susceptible to develop a liver cancer.

Primary liver cancer is a cancer of liver cells, when normal cells in the liver become abnormal and will then destroy adjacent normal tissues, and spread both to other areas of the liver and to organs outside the liver.

Most people who get liver cancer (hepatic cancer) get it in the setting of chronic liver disease. Indeed, the leading cause of liver cancer is cirrhosis due to hepatitis B, hepatitis C, and non-alcoholic (NAFLD) or alcoholic (ALD) fatty liver disease. In fact, advanced fibrosis (F2, F3 or F4 according to METAVIR classification) is present in more than 90% of the primary liver cancer cases.

The most common types are hepatocellular carcinoma (HCC), which makes up 80% of cases, and cholangiocarcinoma. Less common types include mucinous cystic neoplasm and intraductal papillary biliary neoplasm.

The diagnosis is usually supported by medical imaging and use of some blood markers, with confirmation by tissue biopsy.

Imaging modalities include sonography (ultrasound), computed tomography (CT) and magnetic resonance imaging (MRI). Detection of a solid and hypervascularized mass greater than 2 cm with ultrasound is indicative of HCC in 95% of the cases.

Cholangiocarcinomas, occuring in the hilar region of the liver, and often present as bile duct obstruction, are usually detected by endoscopic retrograde cholangiopancreatography (ERCP), ultrasound, CT, MRI and magnetic resonance cholangiopancreatography (MRCP).

The blood marker used for diagnostic of liver cancer is alfa-fetoprotein (AFP), which may be elevated in 70% of patients with liver cancer. However, detection of this protein is not very sensitive as AFP levels could be normal in liver cancer, although a rising level of AFP is generally a sign of liver cancer. One could also look for variation of blood levels of des-gamma-carboxy prothrombin, carbohydrate antigen 19-9 (CA 19-9), carcinoembryonic antigen (CEA) and cancer antigen 125 (CA125). These markers, however, are not very specific.

It is important to detect patients with a high risk of developing liver cancer, in order to be able to propose them regular surveillance. The patients would have a higher relative risk of having a primary liver cancer as compared to the global population of patients. This would thus allow early detection of cancer onset, increased chances to cure it, while decreasing morbidity, and costs of treatment. Being able to determine, in the population of patient with advanced fibrosis, those having a higher risk of developing liver cancer, to propose a regular monitoring and costly treatment of the cause (such as anti-virus C) only to these is an important public health issue.

It is however difficult to propose a detection of primary cancer liver to all patients having chronic liver disease, in view of the relatively low occurrence of such cancer in this population (around 1-2% of the patients). The possibility to segment the population in multiple classes where patients in some classes have a higher risk of having a primary liver cancer than patients of the other classes makes it possible to both reduce the number of prescribed specific medical examinations (imagery) and increase the proportion of positive cases detected in the patients examined.

The present application discloses a new test to detect whether a patient, in particular with a chronic liver disease, has a higher risk of having a primary liver cancer, using a function made by combining the measured values of various biochemical blood markers. This increased risk corresponds to a relative increased risk, i.e. to the fact that the patient is placed in a group in which the global risk of having a primary liver cancer is higher than for patients that are not in this group. In other words, it is possible to determine a threshold which defines two groups (or class) of patients (value of the function below or higher than the threshold). The relative risk of having a primary liver for patients in one of the group will thus be significantly higher than for patients in the other group. The function is quantitative, so the higher the threshold, the higher the relative risk. It is also possible to determine more than one threshold, with relative risks different in each groups (classes) thus constituted.

It is to be noted that the functions herein disclosed were obtained using a population of patients, some of which having liver cancer. It is surprising, however, that this function is not an indicator of the presence or absence of primary liver cancer in patient, but makes it possible to identify patients not having cancer yet, but that have an increased risk of having such.

The quality of a test is generally determined by drawing a Receiving Operating Characteristic (ROC) curve and measuring the Area Under Receiving Operating Characteristic curve (AUROC).

The ROC curve is drawn by plotting the sensitivity versus (1-specificity), after classification of the patients, according to the result obtained for the test, for different thresholds (from 0 to 1).

It is usually acknowledged that a ROC curve, the area under which has a value superior to 0.7, is a good predictive curve. The ROC curve has to be acknowledged as a curve allowing prediction of the quality of a test. It is best for the AUROC to be as closed as 1 as possible, this value describing a test which is 100% specific and sensitive.

It is reminded that (1) sensitivity is the probability that the diagnosis is positive in individuals having the phenotype sought (detection of true positives): the test is positive if the patient is having the phenotype. The sensitivity is low when the number of false negatives is high. The sensitivity is calculated by the formula SE=(number of individuals having the phenotype in whom the sign is present)/(number of individuals having the phenotype in whom the sign is present+number of individuals having the phenotype in whom the sign is absent).

(2) specificity is the probability that the diagnosis is negative in the individuals not having the phenotype sought (non-detection of true negatives): the test is negative if the patient is not suffering from the disease. The specificity is low when the number of false positives is high. The specificity is calculated by the formula SP=(number of individuals not having the phenotype in whom the sign is absent)/(number of individuals not having the phenotype in whom the sign is absent+number of individuals not having the phenotype in whom the sign is present).

(3) Positive predictive value (PPV): is the probability of having the disease if the diagnostic test is positive (i.e. that the patient is not a false positive): the patient is having the phenotype if the test is positive. The positive predictive value is calculated by the formula PPV=(number of individuals having the phenotype in whom the sign is present)/(number of individuals having the phenotype in whom the sign is present+number of individuals not having the phenotype in whom the sign is present).

(4) Negative predictive value (NPV): is the probability of not having the disease if the diagnostic test is negative (that the patient is not a false negative): the patient is not having the phenotype if the test is negative. The negative predictive value is calculated by the formula NPV=(number of individuals not having the phenotype in whom the sign is absent)/(number of individuals not having the phenotype in whom the sign is absent+number of individuals having the phenotype in whom the sign is absent)

In order to obtain a good diagnostic test, it is important to both increase specificity and sensitivity.

In developing the assays and tests as herein disclosed, the inventor increased the sensitivity of the existing tests (Fibrotest only looking at presence of fibrosis and search for AFP as a liver cancer marker). The inventor showed that a better AUROC was obtained by creating the new test as herein described, that is still increased in tests using fibrosis markers and AFP.

Generally, a diagnosis (or prognosis) method comprises
i. a step of gathering information from the patient
ii. a step of comparing said information with regards to thresholds
iii. a step of deducing, from the difference between the patient's information and the threshold, whether the patient has a specific disease, the stage of the patient's disease, or whether the patient's state will evolve to a given state.

As a matter of illustration
i. the information that can be gathered from the patient can be gathered directly from the patient (such as images from NMR, scanner, radiography, contrast-enhanced computed tomography), or indirectly from the patient, such as from a biological sample that has been obtained from a patient (such as urine, blood sample . . . ). The information can be presence (or absence) and/or level of specific biological markers, whether specific from the pathogenic determinant (bacterial or viral DNA/RNA), or elevated levels of patient's markers
ii. once the information is obtained, it is compared to different values/standards and the deviation with regards to these standards is assessed. As a matter of illustration, the level of some biomarkers shall be compared to the level usually observed in healthy patients and to the levels usually observed in patients with the disease (or for patients who have been known to later evolve to a specific disease stage, for prognosis methods). Thresholds may exist, where 95% of patients having passed the threshold have the disease and 95% of the patients not having passed the threshold do not have the disease. For diseases where multiple clinical stages can be determined, such thresholds can discriminate the different stages. In this step ii, one may compare various types of information to their respective standards, in order to be able to reach a diagnostic in step iii (as a matter of illustration, one can use the values and information obtained from measurement of various blood or plasma markers, images from scanner and of Body Mass Index).
iii. the last step is actually making the diagnosis (resp. determining a prognosis) i.e. deciding whether or not the patient has the condition sought resp. whether or not the patient will evolve to a given clinical state), taking, in particular, into account the information gathered from the patient, the thresholds as described above. The physician may also take into account other elements (such as the consistency of the information gathered or the like) to make the diagnostic.

Some methods, such as the ones disclosed in the present application, shall also include a step i.a), which comprise the steps of modifying the information obtained from the patient in order to obtain a new type of information, which is the one that is then compared to the standards in step ii. Such modification is the combination of the values of variables in a function, and obtaining an end value.

It is further to be noted that the mere measurement of the values of levels of markers in the plasma or serum of a patient and the combination thereof in an algorithm as herein disclosed is part of a method but only provides an intermediate result (an end value or index) that would then to be compared to a reference index (threshold), in order to actually be able to pose the diagnostic.

It is also to be noted that the tests herein disclosed are not "gold-standard" tests, in the sense that the output (index calculated by the formulas herein disclosed) isn't a definitive answer as to the state of the patient. Indeed, these tests are based on statistics and there may thus be false-positive or false-negative results, which is the reason why the specific experience of the physician in interpreting the index is of importance for making the prognosis and deciding which kind of follow up is to be made to ne made for each patient.

However, due to the specificity, sensitivity, positive predictive value and negative predictive value of the tests, herein provided for various thresholds of the index, these tests are of great interest in provided a help to the physician when investigating a clinical case. Consequently, step iii as disclosed above is not direct and immediate from step ii, as the physician must interpret the result from the clinical and general context to be able to reach a conclusion.

The present application thus discloses a new test that makes it possible to determine whether a patient will develop a liver cancer over a given period of time (such as in the following 5, 10 or 15 years), especially when the patient has a chronic liver disease.

The methods comprise the step of combining the values as measured from markers present in the blood, serum or plasma of said patient through a function, in order to obtain an end index, which is indicative of a "liver cancer risk class" to which belongs the patient.

This method is performed in vitro, or ex vivo.

This method is particularly interesting in that it makes it possible to manage the follow-up of the patient, and propose further liver cancer diagnosis tests (such as imaging or new specific liver cancer test) only to a fraction of patients that are the most at risk of developing cancer. For other patients, who are not at risk of having a liver cancer in a short (less than 5 years) period, the method can be repeated at a further time, in order to determine whether there is any evolution of the status (of the end value) and whether the risk remains stable or increases (whether the patient's changes risk class). This method thus makes it possible to detect primary liver cancer at early stage and starts treatment, thus reducing mortality, morbidity and associated costs.

Below are described a few functions that can be used for performing the method herein disclosed. It is however to be noted that there is no technical difficulty to obtain and develop other functions that would be as (or more) efficient as the functions herein disclosed, following the teachings of the invention.

It is also to be noted that some functions herein disclosed only makes use of the blood (or plasma or serum) measured values of classical liver markers (fibrosis markers) and don't use the values of liver cancer markers. It is surprising to note that such prognosis of occurrence of cancer can be made without using any cancer-specific marker. This is also very useful, as the "classical" (not comprising liver cancer markers) markers are widely studied by physicians in the art. The use of a function that doesn't comprise liver-cancer markers thus makes it possible for the physician to first assess the risk of the patient and then to request a further blood test to measure the value of the liver cancer marker and refine the test, using the other function herein disclosed.

It is also to be noted that, although the function herein exemplified have been obtained by logistic regression, other statistical methods could be used to obtain the risk of developing primary liver cancer, in particular Cox regression (the hazard being the occurrence of primary liver cancer), which would thus provide other functions having the same kind of output of the logistic regression functions herein exemplified (measure the risk of primary liver cancer occurrence).

Although any markers can be used in the disclosed function, one can choose not to use bilirubin (total bilirubin) an/or transferases (ALT (Alanine Aminotransferase) or AST (Aspartate Aminotransferase)). This is because such markers may widely vary for multiple reasons.

A contrario, it is preferred when the function uses the levels of Haptoglobin and of Apolipoprotein A-I (apoA1).

The invention thus relates to a method for determining whether a patient, in particular presenting chronic liver disease, has a risk of developing a primary liver cancer, comprising the step of combining the values of blood markers as measured in the blood, serum or plasma of the patient through a function combining the values of the blood markers. This method is also a method for monitoring the evolution of a liver disease, performing a follow-up of a patient and may include steps of treating the patient or performing further appropriate diagnostic and/or follow-up tests to the patient.

It is thus possible to obtain an end value, and to compare this end value to a predetermined threshold wherein the patient has a risk of developing a primary cancer liver if the end value is higher/lower than a predetermined threshold.

Indeed, the invention would thus relates to a method for determining whether a patient has a risk of developing a primary liver cancer, comprising the step of combining the values of biochemical markers as measured in the blood, serum or plasma of the patient through a function, obtaining an end value, comparting the end value to predetermined values (thresholds), wherein the variation of the end value to the predetermined values indicates the risk of the patient to develop a primary cancer liver As indicated above, the risk shall be obtained for a given period of time after the test is made, that can span up to 15 years. The figures of the application, although illustrative and pertaining to specific functions, can be used to determine, for any duration up to 15 years, the percentage, in each class of primary liver cancer occurrence and hence the risk of each class. In particular, the risk can be assessed for 5, 10 or 15 years.

The patient preferably has a chronic liver disease, which is preferably selected from the group consisting of infection with the hepatitis B virus, infection with the hepatitis C virus, Non-Alcoholic Fatty Liver disease (NAFLD), Alcoholic liver disease (ALD). The patient may also have NASH disease (Non-alcoholic steatohepatitis).

The blood markers, the amount of which is measured and used in the function, are preferably of liver fibrosis blood markers. This corresponds to blood markers which vary when the patient has a liver disease (fibrosis generally appearing when such disease is present).

The markers can thus be selected from the group consisting of α2-macroglobulin (A2M), GGT (gammaglutamyl transpeptidase), haptoglobin, apolipoprotein A-I (apoA1), bilirubin, alanine transaminases (ALT), aspartate transaminases (AST), triglycerides, total cholesterol, fasting glucose, γ-globulin, albumin, α1-globulin, α2-globulin, β-globulin, IL10, TGF-β1, apoA2, apoB, cytokeratin 18, platelets number, prothrombin level, hyaluronic acid, urea, N-terminal of type III pro-collagen, tissue inhibitor metalloproteinase type-1 (TIMP-1), type IV collagen (Coll IV), osteoprotegerin, miRNA122, cytokeratin-18, serum amyloid A (SAA), alpha-1-antitrypsin (isoform 1), fructose-bisphosphate aldolase A, Fructose-bisphosphate aldolase B, fumarylacetoacetase, transthyretin, PR02275, C-reactive protein (isoform 1), leucine-rich alpha-2-glycoprotein, serpin A11, DNA-directed RNA polymerase I subunit RPA1, obscurin (isoform 1), alpha-skeletal muscle actin, aortic smooth muscle actin, alkaline phosphatase, uncharacterized protein C22orf30 (isoform 4), serum amyloid A2 (isoform a), apolipoprotein C-Ill, apolipoprotein E, apolipoprotein A-II, polymeric immunoglobulin receptor, von Willebrand factor, aminoacylase-1, G-protein coupled receptor 98 (isoform 1), paraoxonase/arylesterase 1, complement component C7, hemopexin, complement C1q subcomponent, paraoxonase/lactonase 3, complement C2 (fragment), versican core protein (isoform Vint), extracellular matrix protein 1 (isoform 1), E3 SUMO-protein ligase RanBP2, haptoglobin-related protein (isoform 1), adiponectin, retinol binding protein, ceruloplasmin, alpha 2 antiplasmin, antithrombin, thyroxin binding protein, protein C, alpha 2lipoprotein, tetranectin, fucosylated A2M, fucosylated haptoglobin, fucosylated apoA1 and carbohydrate deficient transferrin.

Change of the concentration of these markers is associated with non-specific liver injury and these are thus not specifically associated with primary liver cancer.

In a preferred embodiment, the biochemical markers are selected from the group consisting of α2-macroglobulin (A2M), GGT (gammaglutamyl transpeptidase), haptoglobin, apolipoprotein A-I (apoA1), bilirubin, alanine transaminases (ALT), aspartate transaminases (AST), triglycerides, total cholesterol, fasting glucose, cytokeratin 18, platelets number, prothrombin level, hyaluronic acid, amyloid A (SAA), hemopexin and carbohydrate deficient transferrin. This group would also comprise the fucosylated forms of proteins and in particular fucosylated A2M, fucosylated haptoglobin, fucosylated apoA1.

As indicated above, it is also possible to use at least one marker of liver cancer such as α-fetoprotein (AFP), fucosylated AFP, HSP27 (heat shock protein), HSP70, Glypican-3 (GPC3), squamous cell carcinoma antigen (SCCA) and in particular SCCA-IgM IC which is a circulating immune complex composed of SCCA and IgM, Golgi protein 73 (GP73), α-L-fucosidase (AFU), Des-γ-carboxyprothrombin (DCP or PIVKA), Osteopontin (OPN), or Human Carbonyl Reductase. Other hepatocellular carcinoma (HCC) markers are disclosed in particular in Zhao et al Mol Clin Oncol. 2013 July; 1(4): 593-598, Salloom, Int J Health Sci (Qassim). 2016 January; 10(1): 121-136, Tara Behne and Copur, International Journal of Hepatology, vol. 2012, Article ID 859076, 7 pages. Change of concentration of these markers is correlated with primary cancer liver (these markers could thus be considered as specific of liver cancer).

It is to be noted that α-fetoprotein (AFP) is a protein that can be fucosylated or not, and has three glycoforms (AFP-L1, AFP-L2 and AFP-L3), named according to their binding ability to the lectin lens agglutinin (LCA). It is possible to detect any form of the AFP protein, alone or combinations of such isoforms. In particular, combined detection of AFP and AFP-L3 (the *Lens culinaris* agglutinin-reactive fraction of alpha-fetoprotein) can be made.

It is thus possible use a function that uses the values of serum markers of liver disease as indicated above and of at least one cancer marker.

It is also possible to include, as variable in the function, at least one other variable chosen in the group consisting of gender, age and BMI (Body Mass Index) of the patient. Fasting glucose levels could also be used.

As indicated above, the function that can be used in the method herein disclosed can be a function obtained by logistic regression (which can be called logistic function).

Methods to perform logistic regressions are known in the art. In summary, they consist in evaluating the individual variations of markers between populations of subjects (one with the output such as the liver cancer and the other where the output is absent). The markers which are the most variable can be chosen and logistic regression analysis is made to ponder the independent discriminative value of the selected markers. If some markers don't vary between groups, the coefficients of these markers in the function will be low (thereby indicating that the weight of these markers is of no real influence for the presence of the trait).

The function can then be normalized (for example to have the end result always comprised between 0 and 1).

In the present invention, the function can be obtained by any of the methods disclosed below, and in particular by
a) evaluating the presence of liver cancer after a given duration of time in a cohort of patients, preferably presenting chronic liver disease, wherein the values of the blood markers variables used in the function are known for the patients at the beginning of the duration of time
b) identifying by unidimensional analysis, among the blood markers, the value of which has been measured, the ones for which the values differ significantly between the groups of
i. patients with liver cancer and
ii. patients without liver cancer
c) performing a logistic regression analysis to assess and ponder the independent discriminative value of the markers identified in step b) for the occurrence of liver cancer in the given duration of time
d) thereby obtaining the function, by combination of these identified independent factors.

In order to obtain a function that is as accurate as possible, the number of patients in the cohort should be as large as possible, indicating that it preferably comprises more than 50 patients, preferably more than 100 patients, preferably more than 200 patients, more preferably more than 500 patients, or even more than 1000 patients. As indicated, there is no upper limit for the number of patients, and the larger, the better.

The duration of time is chosen by the person skilled in the art. If one desires that the function is indicative of the occurrence of cancer liver at five years, the duration of time shall be 5 years. This means that the groups of b) will be the patients with liver cancer after 5 years and the patients without liver cancer after 5 years. Other time periods can be used (10, 15 years or more). In the present application, the disclosed functions have been designed with a 15 years period. It is striking to note that these functions are nevertheless indicative of a primary liver cancer risk at lower duration of time (5 and 10 years). However, other functions could have been designed by the inventors, with other endpoint durations, which may be more accurate for these specific endpoints, In particular, the inventor has shown that it is possible to obtain an accurate function, using the values measured for alpha-2-macroglobulin (A2M), apoA1, GGT and haptoglobin. In a more specific embodiment, the function doesn't include the values of other markers of blood, serum or plasma. In other words, the only values of blood, serum or plasma markers that are used within the logistic function are the values measured for apoA1, A2M, GGT and haptoglobin.

The function may further include at least one other variable chosen in the group consisting of gender, age and BMI of the patient. In this embodiment, the logistic function will use both the values of the markers from blood, serum or plasma and the value measured from at least one of the other variable as recited above. It is preferred when the logistic function further takes into consideration both the gender (sex) and the age of the patient.

Consequently, a function, as usable in the context of the present invention, may have the form:

F1=a0+a1×Log (A2M, g/l)+a2×Age (years)+a3×ApoA1 (g/l)+a4×Gender (0 for women, 1 for men)+a5×Log(GGT, IU/l)+a6×Log (Hapto, g/l).

In this embodiment, $-6 \le a0 \le -3.4$ preferably $-5.2 \le a0 \le -4.7$ $2.4 \le a1 \le 4.6$ preferably $3 \le a1 \le 4$ $0.02 \le a2 \le 0.07$ preferably $0.03 \le a2 \le 0.07$ $2.6 \le a3 \le -0.8$ preferably $-2.2 \le a3 \le -1.0$ $1.5 \le a4 \le -0.5$ preferably $-1.2 \le a4 \le -0.6$ $0.9 \le a5 \le 1.9$ preferably $1.2 \le a5 \le 1.7$ $1.5 \le a6 \le -0.5$ preferably $-1.1 \le a6 \le -0.6$.

In a preferred embodiment, the function is
F1-a=−4.819+3.673×Log A2M (g/L)+0.053×Age (years)−1.983×ApoA1 (g/L)−1.122×Sex (0 for women, 1 for men)+1.603×Log GGT (IU/L)−0.834×Log Hapto (g/L).

Such function for the diagnosis of contemporaneous liver cancer (current presence of liver cancer) has an AUROC value of 0.915 vs 0.896 for the FibroTest AUROC, an AUROCs difference of 0.019 (95% CI; 0.005-0.033; P=0.0001), i.e. a 2% difference and increase of both specificity and sensitivity (FIG. 1).

In another embodiment, the function is:
F1-b=−4.982+3.713×Log A2m (g/L)+0.0473×Age (years)−1.133×ApoA1 (g/L)−0.791×Sex (0 for women, 1 for men)+1.343×Log GGT (IU/L)−1.062×Log Hapto (g/L).

The function herein disclosed will provide an end result (index or score) that is compared to a threshold to determine the class of patients to which the patient belongs.

As an illustration, for function F1-a, if the end result is below 0.25, the patient belongs to the class "low cancer risk), indicating that the risk of having a primary liver cancer is 0.9792 (there would be 208 primary liver cancer cases in a population of 10000 patients having an index below 0.25).

If the end result is higher than 0.25, the patient belongs to the class "high cancer risk), indicating that the risk of having a primary liver cancer is 0.8449 (there would be 1551 primary liver cancer cases in a population of 10000 patients having an index above or equal to 0.25).

The relative risk between the two classes is thus more than 7 times higher in the group of patients having an index higher or equal to 0.25.

Consequently, in this case, setting the threshold as 0.25 makes it possible to detect patients belonging to a group with an increased risk to develop a primary liver cancer, said group consisting of patients having an end result is higher or equal to 0.25.

It is also possible to set up other thresholds and thus design other groups (classes) of patients with an increased risk to develop a primary liver cancer. As an illustration, one can design groups of patients having an end result is higher or equal to 0.25 and lower than 0.50, or higher or equal to 0.50 and lower than 0.75, or greater or equal to 0.75.

If the end result is higher than 0.25 and lower than 0.50, the patient belongs to the class "moderate cancer risk", indicating that the risk of having a primary liver cancer is 0.9124 (there would be 876 primary liver cancer cases in a population of 10000 patients having an index above or equal to 0.25 and lower than 0.50).

If the end result is higher than 0.50 and lower than 0.75, the patient belongs to the class "intermediate cancer risk", indicating that the risk of having a primary liver cancer is 0.8225 (there would be 1,775 primary liver cancer cases in a population of 10000 patients having an index above or equal to 0.25 and lower than 0.50). The relative risk in this class is thus twice the risk of the "moderate cancer risk" class.

If the end result is higher than 0.75, the patient belongs to the class "very high cancer risk", indicating that the risk of having a primary liver cancer is 0.6933, meaning that there would be 3067 primary liver cancer cases in a population of 10,000 patients having an index above or equal to 0.75 (a relative risk of more than 14 with regards to the "low cancer risk" class).

It is also possible to design and use functions where primary liver cancer markers are also used. In particular, the inventor showed that addition of AFP to the other markers makes it possible to design functions as or more efficient than functions that don't incorporate these markers. It is also to be noted that the non-specific markers and the specific cancer markers can be combined in the same function or used in independent juxtaposition analysis.

Thus, a function may be:
F2=a0+a1×Log (A2M, g/l)+a2×Age (years)+a3×ApoA1 (g/l)+a4×Gender (0 for women, 1 for men)+a5×Log(GGT, IU/l)+a6×Log (Hapto, g/l)+a7×Log AFP (µg/L).

In such function,
a) $-7 \leq a0 \leq -5.5$ preferably $-6.5 \leq a0 \leq -6$
b) $2.2 \leq a1 \leq 3.2$ preferably $2.5 \leq a1 \leq 2.9$
c) $0.02 \leq a2 \leq 0.06$ preferably $0.04 \leq a2 \leq 0.05$
d) $-1.65 \leq a3 \leq -1.25$ preferably $-1.55 \leq a3 \leq -1.35$
e) $-0.3 \leq a4 \leq -0.22$ preferably $-0.28 \leq a4 \leq -0.24$
f) $1.25 \leq a5 \leq 1.85$ preferably $1.45 \leq a5 \leq 1.65$
g) $-0.75 \leq a6 \leq -0.55$ preferably $-0.7 \leq a6 \leq -0.6$
h) $1.3 \leq a7 \leq 1.9$ preferably $1.5 \leq a7 \leq 1.8$ The function may be
F2-a=−6.214+2.713 Log A2m (g/L)+0.0447×Age (years)−1.451×ApoA1 (g/L)−0.260×Sex (0 for women, 1 for men)+1.557×Log GGT (IU/L)−0.633×Log Hapto (g/L)+1.662×Log AFP (µg/L).

As indicated above the function may be a (multivariate) Cox function. Such Cox function is preferably obtained by
a) Assessing/evaluating the presence of liver cancer after a given duration of time in patients presenting chronic liver disease, wherein the values of the variables used in the function are known at the beginning of the duration of time
b) Performing a multivariate Cox regression by combination of said values, on the basis of the occurrence of liver cancer after the given duration of time
c) Assessing the independent discriminative value of the values by analysis of the multivariate Cox regression,
d) Combining the relative weight of the values of each marker, as individually determined in the multivariate Cox regression, with a negative sign when the markers harbor a negative correlation with the observation of liver cancer occurrence.

The markers that can be used in this method are the same as disclosed above. The period of time is chosen by the one of skill in the art, and is generally multiple years (such as 5, 10 15 years).

As examples of Cox functions usable in the context of the present invention are:
C1=b1×ApoA1 (g/L)−b2×Log Hapto (g/L)+b3×Log GGT (IU/L)+b4×Log A2m (g/L)+b5×Age (years)+b6×Sex (0 for women, 1 for men).

With $0.6 \leq b1 \leq 0.8$ $1.0 \leq b2 \leq 1.1$ $1.4 \leq b3 \leq 1.5$ $2.6 \leq b4 \leq 2.7$ $0.05 \leq b5 \leq 0.07$ $0.8 \leq b6 \leq 1.1$ In particular, a function can be (with an approximation at the $5^{th}$ decimal):
C1-a=0.67930×ApoA1 (g/L)−1.02404×Log Hapto (g/L)+1.46545×Log GGT (IU/L)+2.65740×Log A2m (g/L)+0.06346×Age (years)+0.97350×Sex (0 for women, 1 for men).

C1-b=0.67930×ApoA1 (g/L)−1.05404×Log Hapto (g/L)+1.46545×Log GGT (IU/L)+2.65740×Log A2m (g/L)+0.06346×Age (years)+0.97350×Sex (0 for women, 1 for men).

These functions are particularly interesting to determine the risk of liver cancer at 10 years.

Another function is
C2=c1×Log AFP (µg/L)−c2×ApoA1 (g/L)−c3×Log Hapto (g/L)+c4 Log GGT (IU/L)+c5×Log A2m (g/L)+c6×Age (years)+c7×Sex (0 for women, 1 for men).

With $0.8 \leq c1 \leq 1.0$ $0.7 \leq c2 \leq 0.9$ $0.5 \leq c3 \leq 0.7$ $1.1 \leq c4 \leq 1.3$ $1.4 \leq c5 \leq 1.5$ $0.06 \leq c6 \leq 0.08$ $0.4 \leq c7 \leq 0.6$ In particular, a function can be (with an approximation at the 5$^{th}$ decimal):

C2=0.88166×Log AFP (μg/L)−0.82480×ApoA1 (g/L)−0.62809×Log Hapto (g/L)+1.20973 Log GGT (IU/L)+1.42462×Log A2m (g/L)+0.07235×Age (years)+0.53213×Sex (0 for women, 1 for men).

Another function that is particularly interesting for assessing the risk of liver cancer at 5 years is C3=d1×Log AFP (μg/L)−d2×ApoA1 (g/L)−d3×Log Hapto (g/L)+d4 Log GGT (IU/L)+d5×Log A2m (g/L)+d6×Age (years)+d7×Sex (0 for women, 1 for men).

With $0.6 \leq c1 \leq 0.8$ $1.0 \leq c2 \leq 1.2$ $0.7 \leq c3 \leq 0.9$ $1.1 \leq c4 \leq 1.3$ $1.3 \leq c5 \leq 1.5$ $0.06 \leq c6 \leq 0.09$ $0.2 \leq c7 \leq 0.4$ In particular, a function can be (with an approximation at the 5$^{th}$ decimal):

C3=0.68030×Log AFP (μg/L)−1.13208×ApoA1 (g/L)−0.82013×Log Hapto (g/L)+1.20152 Log GGT (IU/L)+1.39771×Log A2m (g/L)+0.07582×Age (years)+0.31238×Sex (0 for women, 1 for men).

The function may be used as follows:

Presence of cirrhosis in a patient is determined by any method known in the art (Fibrotest®, formula f5 in WO 02/16949; Transient elastography such as Fibroscan®).

If the patient has cirrhosis, he has already a risk for primary liver cancer and the physician shall monitor for this risk according to the currently standard methods (imaging, dosage of AFP generally every 6 months). Other methods for monitoring the appearance of liver cancer may also be used.

If the patient doesn't have any cirrhosis marker, C1-a or C1-b shall be performed. If the result is below the median (around 0.039), due to the high Negative Predictive Value of these formulas, the patient shall only be treated for his liver disease whatever it is. If the result is above or equal to the median (around 0.039), C3 shall be performed.

If the value of C3 is below the median (around 0.026), due to the high Negative Predictive Value of these formulas, the patient shall only be treated for his liver disease whatever it is. Fibrotest (or Fibroscan), C1-a, C1-b and C3 (if needed) may also be performed on a regular basis in the follow-up. If the result is above or equal to the median, the patient should be considered as if he has cirrhosis and the physician shall monitor for primary liver cancer according to the available methods (imaging, dosage of AFP generally every 6 months).

Although the present application discloses a function that can be used in the methods herein proposed, the present invention also relates to a method for obtaining functions that can assist a physician to determine whether a patient, in particular with chronic liver disease is at risk of developing a primary liver cancer wherein said logistic function combines the values of the concentration of biochemical markers in the serum of said patient. Thus, depending on the markers that are chosen by the person skilled in the art, other functions than the ones herein disclosed can be obtained.

The art already describes different means making it possible to obtain a function by logistic regression, the end value of which is indicative of the degree of liver fibrosis. In particular, one can cite WO 2002/016949, and different declinations of the method first described in WO 2002/016949: WO 2010/149767, WO 2006/10357, WO 2006/082522, WO 2003/073822, WO 2011/039321, WO 2005/116901, WO 2010/058295, and WO 2010/097472.

In the present case, the end value of the function obtained by the method disclosed below is indicative of the risk for the patient to have a primary liver cancer.

The invention thus relates to a method for obtaining a function that can assist a physician to determine whether a patient, in particular with chronic liver disease is at risk of developing a primary liver cancer after a given period of time, wherein said function combines the values of the concentration of biochemical markers in the blood/serum or plasma of said patient and optionally the age, gender and BMI, comprising the steps of:
   a) classifying patients of a cohort of patients into two groups according to the presence or absence of primary liver cancer after a given period of time
   b) identifying by unidimensional analysis, the biochemical markers, the value of which has been measured in the patients at the beginning of the given period of time, the ones which differs significantly between the group of patients in which cancer has occurred and the group of patients in which cancer has not occurred
   c) performing a logistic regression analysis to assess the independent discriminative value of these markers identified in step b) for the occurrence of primary liver cancer
   d) obtaining the function by combination of these identified independent factors.

In another embodiment, the invention thus relates to a method for obtaining a function that can assist a physician to determine whether a patient, in particular with chronic liver disease is at risk of developing a primary liver cancer wherein said function combines the values of the concentration of biochemical markers in the blood/serum or plasma of said patient and optionally the age, gender and BMI, comprising the steps of:
   a) classifying patients of a cohort of patients into two groups according to the presence or absence of primary liver cancer in the patients
   b) identifying by unidimensional analysis, the biochemical markers, the value of which has been measured in the patients, the ones which differs significantly between the group of patients having primary liver cancer and the group of patients not having primary liver cancer
   c) performing a logistic regression analysis to assess the independent discriminative value of these markers identified in step b) for the occurrence of primary liver cancer
   d) obtaining the function by combination of these identified independent factors.

This method differs from the one disclosed just before, that the function is here designed on contemporaneous liver cancer, where it there is designed on primary liver cancer as they appear during the given period of time.

For both methods, the thresholds making it possible to classify the patients within risk classes are determined by classical statistical methods.

The functions herein disclosed have been designed on the basis of the second method (using contemporaneous cancers) and have proven to be predictive of the risk of developing cancer in the future, as shown in the examples. The fact that such test is predictive is thus unexpected, as it could have been expected that the function would be indicative of the contemporaneous presence of liver cancer, but it could not have been predicted that the function would be able to predict future occurrence (more than one year after performing the test) of liver cancer.

It is preferred when the biochemical markers of step b) are selected from the group consisting of α2-macroglobulin (A2M), GGT (gammaglutamyl transpeptidase), haptoglobin, apolipoprotein A-I (apoA1), bilirubin, alanine transaminases (ALT), aspartate transaminases (AST), triglycerides, total cholesterol, fasting glucose, γ-globulin, albumin, α1-globulin, α2-globulin, β-globulin, IL10, TGF-β1, apoA2, apoB, cytokeratin 18, platelets number, prothrombin level, hyaluronic acid, urea, N-terminal of type III pro-collagen, tissue inhibitor metalloproteinase type-1 (TIMP-1), type IV collagen (Coll IV), osteoprotegerin, miRNA122, cytokeratin-18, serum amyloid A (SAA), alpha-1-antitrypsin (isoform 1), fructose-bisphosphate aldolase A, Fructose-bisphosphate aldolase B, fumarylacetoacetase, transthyretin, PR02275, C-reactive protein (isoform 1), leucine-rich alpha-2-glycoprotein, serpin A11, DNA-directed RNA polymerase I subunit RPA1, obscurin (isoform 1), alpha-skeletal muscle actin, aortic smooth muscle actin, alkaline phosphatase, uncharacterized protein C22orf30 (isoform 4), serum amyloid A2 (isoform a), apolipoprotein C-Ill, apolipoprotein E, apolipoprotein A-II, polymeric immunoglobulin receptor, von Willebrand factor, aminoacylase-1, G-protein coupled receptor 98 (isoform 1), paraoxonase/arylesterase 1, complement component C7, hemopexin, complement C1q subcomponent, paraoxonase/lactonase 3, complement C2 (fragment), versican core protein (isoform Vint), extracellular matrix protein 1 (isoform 1), E3 SUMO-protein ligase RanBP2, haptoglobin-related protein (isoform 1), adiponectin, retinol binding protein, ceruloplasmin, alpha 2 antiplasmin, antithrombin, thyroxin binding protein, protein C, alpha 2lipoprotein, tetranectin, fucosylated A2M, fucosylated haptoglobin, fucosylated apoA1 and carbohydrate deficient transferrin.

It is preferred when the biochemical markers of step b) are selected from the group consisting of α2-macroglobulin (A2M), GGT (gammaglutamyl transpeptidase), haptoglobin, apolipoprotein A-I (apoA1), bilirubin, alanine transaminases (ALT), aspartate transaminases (AST), triglycerides, total cholesterol, fasting glucose, cytokeratin 18, platelets number, prothrombin level, hyaluronic acid, amyloid A (SAA), hemopexin and carbohydrate deficient transferrin. This group would also comprise the fucosylated forms of proteins and in particular fucosylated A2M, fucosylated haptoglobin, fucosylated apoA1.

It is also possible to use at least one marker of liver cancer such as α-fetoprotein (AFP), fucosylated AFP, HSP27 (heat shock protein), HSP70, Glypican-3 (GPC3), squamous cell carcinoma antigen (SCCA) and in particular SCCA-IgM IC which is a circulating immune complex composed of SCCA and IgM, Golgi protein 73 (GP73), α-L-fucosidase (AFU), Des-γ-carboxyprothrombin (DCP or PIVKA), Osteopontin (OPN), or Human Carbonyl Reductase, for obtaining the function.

It is preferred when one selects at least or exactly two, at least or exactly three, at least or exactly four, at least or exactly five or at least or exactly six of these markers, although there is no upper limit in the number of markers that can be used in the described methods.

It is however preferred to use a relatively small number of markers, in order to reduce the costs of performing the prognosis method (reduce the cost of blood analysis). Consequently, using three, four or five markers is preferred.

The function may further include at least one other variable chosen in the group consisting of gender, age and BMI of the patient. Fasting glucose level could also be used. However, one will rather use gender and age, as these are easy to determine, while there might be some variability in the BMI or fasting glucose (the patient may not provide the right weight or have eaten before blood harvest).

In another embodiment, it is possible to obtain the function which combines the values of the concentration of biochemical markers in the blood/serum or plasma of said patient and optionally the age, gender and BMI, comprising the steps of:
a) classifying patients of a cohort of patients into two groups according to the presence or absence of primary liver cancer in the patients, after a given period of time
b) providing
  i. the indexes (or scores) obtained for the patients, at the beginning of the given period of time, wherein the indexes method as indicated above to obtain a first function combining the values of the concentration of biochemical markers in the blood/serum or plasma of said patient and optionally the age, gender and BMI, wherein the biochemical markers preferably do not comprise an marker for primary liver cancer
  ii. the value of the level of a marker for primary liver cancer, at the beginning of the given period of time
c) performing a logistic regression analysis to assess the independent discriminative value of the variables i. and ii. of step b) for the occurrence of primary liver cancer
d) obtaining the function by combination of these variables.

Alternatively, it is possible to obtain the function which combines the values of the concentration of biochemical markers in the blood/serum or plasma of said patient and optionally the age, gender and BMI, comprising the steps of:
a) classifying patients of a cohort of patients into two groups according to the presence or absence of primary liver cancer in the patients
b) providing
  i. the indexes (or scores) obtained for the patients, wherein the indexes method as indicated above to obtain a first function combining the values of the concentration of biochemical markers in the blood/serum or plasma of said patient and optionally the age, gender and BMI, wherein the biochemical markers preferably do not comprise an marker for primary liver cancer
  ii. the value of the level of a marker for primary liver cancer
c) performing a logistic regression analysis to assess the independent discriminative value of the variables i. and ii. of step b) for the occurrence of primary liver cancer
d) obtaining the function by combination of these variables.

It is preferred when the biochemical markers of that were used to obtain the function of used in b)i. are selected from the group consisting of α2-macroglobulin (A2M), GGT (gammaglutamyl transpeptidase), haptoglobin, apolipoprotein A-I (apoA1), bilirubin, alanine transaminases (ALT), aspartate transaminases (AST), triglycerides, total cholesterol, fasting glucose, γ-globulin, albumin, α1-globulin, α2-globulin, β-globulin, IL10, TGF-β1, apoA2, apoB, cytokeratin 18, platelets number, prothrombin level, hyaluronic acid, urea, N-terminal of type III pro-collagen, tissue inhibitor metalloproteinase type-1 (TIMP-1), type IV collagen (Coll IV), osteoprotegerin, miRNA122, cytokeratin-18, serum amyloid A (SAA), alpha-1-antitrypsin (isoform 1), fructose-bisphosphate aldolase A, Fructose-bisphosphate aldolase B, fumarylacetoacetase, transthyretin, PR02275, C-reactive protein (isoform 1), leucine-rich alpha-2-glycoprotein, serpin A11, DNA-directed RNA polymerase I subunit RPA1, obscurin (isoform 1), alpha-skeletal muscle actin, aortic smooth muscle actin, alkaline phosphatase, uncharacterized protein C22orf30 (isoform 4), serum amyloid A2 (isoform a), apolipoprotein C-Ill, apolipoprotein E, apolipoprotein A-II, polymeric immunoglobulin receptor, von Willebrand factor, aminoacylase-1, G-protein coupled receptor 98 (isoform 1), paraoxonase/arylesterase 1, complement component C7, hemopexin, complement C1q subcomponent, paraoxonase/lactonase 3, complement C2 (fragment), versican core protein (isoform Vint), extracellular matrix protein 1 (isoform 1), E3 SUMO-protein ligase RanBP2, haptoglobin-related protein (isoform 1), adiponectin, retinol binding protein, ceruloplasmin, alpha 2 antiplasmin, antithrombin, thyroxin binding protein, protein C, alpha 2lipoprotein, tetranectin, fucosylated A2M, fucosylated haptoglobin, fucosylated apoA1 and carbohydrate deficient transferrin, and more preferably selected from the group consisting of α2-macroglobulin (A2M), GGT (gammaglutamyl transpeptidase), haptoglobin, apolipoprotein A-I (apoA1), bilirubin, alanine transaminases (ALT), aspartate transaminases (AST), triglycerides, total cholesterol, fasting glucose, cytokeratin 18, platelets number, prothrombin level, hyaluronic acid, amyloid A (SAA), hemopexin and carbohydrate deficient transferrin. This group would also comprise the fucosylated forms of proteins and in particular fucosylated A2M, fucosylated haptoglobin, fucosylated apoA1.

The at least one marker of liver cancer of b)ii. is preferably selected from the group consisting of α-fetoprotein (AFP), fucolsylated AFP, HSP27 (heat shock protein), HSP70, Glypican-3 (GPC3), squamous cell carcinoma antigen (SCCA) and in particular SCCA-IgM IC which is a circulating immune complex composed of SCCA and IgM, Golgi protein 73 (GP73), α-L-fucosidase (AFU), Des-γ-carboxyprothrombin (DCP or PIVKA), Osteopontin (OPN), and Human Carbonyl Reductase.

In the above methods, the cohort of patients should contain a number of patients high enough so as to ensure robust statistical analysis. It would thus contain at least 50, more preferably at least 100, ore preferably at least 250, more preferably at least 500 patients.

In the above methods, the combination of step d) is made using the coefficients calculated in step c), which depend on the discriminative values as identified in step c). Other steps can be performed, such as normalization of the function to maintain the end results within two selected boundaries.

The method herein disclosed thus makes use of an ex vivo combination of value of different variables, in order to obtain an end-result that is indicative of the risk of primary liver cancer occurrence. It would thus exclude any step applied on the human body of the patient. In the method herein disclosed, it is understood that the markers, the value of which is measured and used as variable in the function, are circulating proteins or natural elements that are present in the blood, plasma or serum of a patient. The values of the chosen markers shall be measured on a sample of blood, plasma or serum previously harvested, according to methods known in the art. The values are expressed in the units according to the art. However, should other units be chosen by the person skilled in the art to expressed the measured values, this would only change the coefficients within the logistic function. The method would thus still be applicable.

However, in another embodiment, the invention relates to a method for prognosis of the occurrence of primary liver cancer in a patient (in particular with chronic liver disease), comprising the step of harvesting blood, plasma or serum from a patient, measuring the value of markers present in the harvested sample and combining the values as measured through a function as disclosed above. The markers are as disclosed above.

The method and functions as herein disclosed may be used to determine the individual risk of a patient to develop PLC (primary liver cancer) during the follow-up of its chronic liver disease. It is thus usually used when the patient already presents a chronic liver disease. It could also be used during routine follow up, so as to provide an assistance for the physician to decide to start a monitoring through imaging, or to treat earlier the patient by a costly antiviral drug usually only prescribed for severe stages of chronic hepatitis C.

The invention also relates to a device for the prognosis of the risk of a patient to have a primary liver cancer, comprising a first means, wherein the first means provides an index by combining the values as measured from markers present in the serum or plasma of a patient (and optionally age and sex) through a function.

The functions and markers to be implemented within this device are the ones disclosed in the present specification. As herein disclosed the device preferably makes it possible to obtain the index using the functions F1, and in particular F1-a or F-1b disclosed above.

In another embodiment, the device makes it possible to obtain the index using the functions F2, and in particular F2a disclosed above.

In another embodiment, the invention relates to a microprocessor comprising a computer algorithm to perform a method of determining the risk of a patient to have a primary liver cancer: providing the values of blood markers of a patient and optionally the age and a value allocated to the sex of the patient; and performing a mathematical function (as disclosed above, or obtained as disclosed above) to combine the values to obtain a score useful for the prognosis of the risk of primary liver cancer occurrence in the patient.

The invention also relates to the use of the functions, devices and/or microprocessors in order to make a diagnosis of presence of a primary liver cancer in a patient by use of the functions and comparing the result to a predetermined threshold to determine the presence of the primary liver cancer in the patient.

With the results of the function, the physician would be able to propose a personalized follow-up to patients, depending on their risk to have a liver cancer.

If patients are F2 or F3 (METAVIR classification) and the score of the test is below 0.25, patients would generally be seen again 3 to 4 years later, and new tests (Fibrotest, Liver cancer test) would be made again.

If patients are F4 (METAVIR, indicating presence of cirrhosis) and the score is <0.25, the normal follow-up would be made (every 3 to 6 months).

If the score is >=0.25, there is a risk of liver cancer. Surveillance on the basis of imaging (at intervals determined by the physician) would thus be proposed, in order to have early detection of cancer occurrence, and treat it early to limit the risks of relapses, mortality and morbidity. Imaging can be proposed to people with higher risk, so as to avoid making clinical exams having low added value (avoiding having a lot of negative results for very few positive results). By only using patient belonging to the risk class, one can increase the proportion of positive cases that are detected. It is also to be noted that the physician may decide to propose, on a regular basis, new blood tests to people in the risk class but having a score close to 0.25 (such as a score between 0.25 and 0.50) and start imaging only if the score is above 0.50 (this number being given as an illustration, the actual number being chosen by the physician).

It is also to be noted that the thresholds herein provided are only for the functions disclosed in details in this application, and that other threshold would be used for other functions.

The invention also pertains to a method for following-up a patient for determining occurrence of primary liver cancer in a patient with (preferentially chronic) liver disease, comprising the steps of
  (1) optionally determine whether the patient has cirrhosis (this can be done by any test available in the art, such as Fibrotest®)
  (2a) if the patient has cirrhosis, make surveillance (imaging and either dosage of AFP or dosage of HR2c or of a function as developed herein containing biochemical markers as herein disclosed and at least a marker for cancer)
  (2b) if the patient has not cirrhosis, perform HR1c (or a function as developed herein containing biochemical markers as herein disclosed but no marker for cancer)
  (3a) if the value of HR1c is below the median, do not perform other specific surveillance, and follow and/or treat the patient on a regular basis for his liver disease
  (3b) if the value of HR1c is higher or equal to the median, then perform surveillance as disclosed above
  (4a) if the imaging data is normal and either the AFP value (if measured) is normal, or the value of HR2c (if measured) is below the median, do not perform other specific surveillance, and follow and/or treat the patient on a regular basis for his liver disease with new surveillance about 6 months later,
  (4b) in presence of at least one of the following
    i) the imaging is not normal, or
    ii) the AFP value (if measured) is not normal, or
    iii) the value of HR2c is higher or equal to the median,
    then make extensive investigation for HCC or CC diagnosis and treatment.

The invention thus also relates to a method for treating a patient in need thereof, comprising the steps of:
  1. Performing the methods are herein disclosed to identify whether the patient has a primary liver cancer, or has a high risk of developing a primary liver cancer, and
  2. Applying a treatment regimen to the patient in need thereof according to the presence of primary liver cancer, or the risk of developing primary liver cancer.

The treatment regimen of step 2) may be one or a combination of:
  Performing surgery or non surgical methods (radio-frequency, intra arterial chemo-embolization . . . ) to remove cancerous mass from the liver
  Providing antitumoral drugs to the patient
  Performing imagery
  Setting up a schedule for follow-up of the patient.
  Providing very early treatment of the chronic liver disease such as direct antiviral agents in CHC (chronic hepatitis C), CHB (chronic hepatitis B), or NAFLD-treatment.

In summary, the present methods provide an easy-to-use blood test making it possible to identify patients with a very high risk of liver cancer, so that they can state-of-the-art imaging techniques that are able to localize very small cancers.

The following examples are meant to describe an aspect of invention, but shall not be limiting the invention.

EXAMPLES

Figure 1:
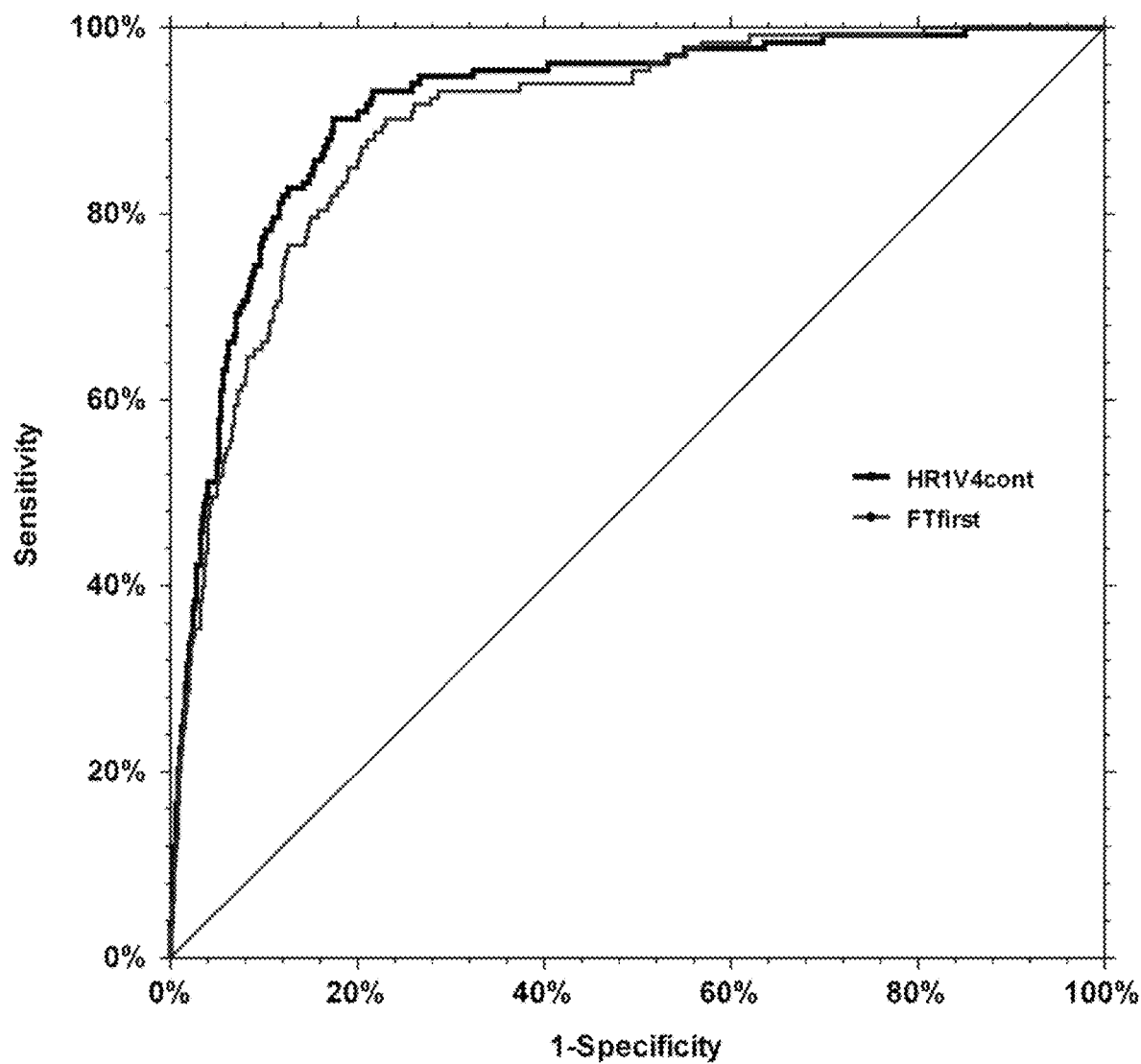
FIG. 1: Compared AUROC (Area Under Receiving Operator Curve) for detection of contemporaneous primary liver cancer from function F1-a (HR1V4) and Fibrotest (FTfirst) (disclosed as f5 in WO 02/16949)

The examples describe embodiments that are fully part of the invention.

Example 1. Methods

Functions were obtained on a cohort of 9,925 patients with chronic liver diseases (named pre-inclusion population)

who all had a FibroTest measurement (Fibrotest as disclosed in WO 2002/016949). Since the Fibrotest formula is 4.467×Log(Alpha2Macroglobulin (g/l))−1.357×Log(Haptoglobin (g/l))+1.017×Log(GGT (IU/l))+0.0281×Age (in years)+1.737×Log(Bilirubin (pmol/1))−1.184×ApoA1 (g/l)+0.301×Sex (female=0, male=1)−5.540, this ensured that measurements of levels of Alpha2Macroglobulin, Haptoglobin, GGT, age (at the time of Fibrotest was performed), Bilirubin, ApoA1 and Sex were available. Furthermore, patients were pre-included only if they had not had previous liver transplantation, and no PLC history.

Primary Liver Cancer was defined as hepatocellular (HCC) or cholangiocarcinoma (CC) according to biopsy, or if missing, Barcelona criteria, or death certificate.

In the construction population (named P0 population), the various mathematical functions, such as f1-a, f1-b and f2-a were obtained by logistic regression, as explained in the specification, using Alpha2Macroglobulin, Haptoglobin, GGT, age (at the time of Fibrotest measurement), Bilirubin, ApoA1 and Sex. Only contemporaneous PLC were taken into account. The performances of functions were assessed using their AUROCs for the diagnostic of contemporaneous PLC.

The prognostic values of the tests were assessed using AUROC and Cox model, in a second population P1 (named longitudinal validation population), with patients who did not develop PLC at least 1 year after the baseline test. This ensured that the analysis is not biased by contemporaneous liver cancers, and that the score is a good prognosis score for occurrence of primary liver cancer.

One internal validation population was used, (named P2 population), a subpopulation of P1 with at least 2 repeated tests (two repeated measurement of biochemical markers) to assess intra-patient variability.

A total of 9,700 patients were included in P0 with
33.9% Chronic Hepatitis C (CHC),
20.5% Chronic Hepatitis B (CHB),
10.8% Non Alcoholic Fatty Liver Disease (NAFLD),
4.8% Alcoholic Liver Disease (ALD)
30.0% mixed or other causes Presence of 134 contemporaneous PLC in P0 (129 hepatocellular, 5 cholangiocarcinoma).

A total of 9,791 patients were included in P1 with presence of 225 incident PLC (216 hepatocellular 9 cholangiocarcinoma), observed within 15 years. Taking into account the patients lost during that time span one can calculate a 15 year-survival without PLC (SwC)=90% (95% CI: 88-92).

A total of 1,773 patients were included in P2 (58 incident PLC with at least 2 repeated tests (7.2 (5.8-6.2) years later), leading to a 15-years SwC 81% (95% CI 72-91)).

Example 2. Evaluation of the Functions

Determination of the Diagnosis Ability of the Function

In P0, HR-Test, a combination of three proteins, one liver function test, age and gender depicted as f1-a, had an AUROC=0.915 (0.889-0.936).

In P1, HR-Test retrieved significant AUROC=0.828 (0.803-0.850), as well as in P2 for paired cases:=0.812 (C1 0.772-0.846).

Further Data as Shown on Figures—Determination of the Prognosis Ability of the Functions From FIG. 1, one can see that a blood test using the same markers (HR1V4) than the ones of Fibrotest (using actually less biochemical markers) is more sensitive and specific than Fibrotest for detecting presence of primary liver cancer (contemporaneous liver cancer), as attested by a higher AUROC.

Figure 2:
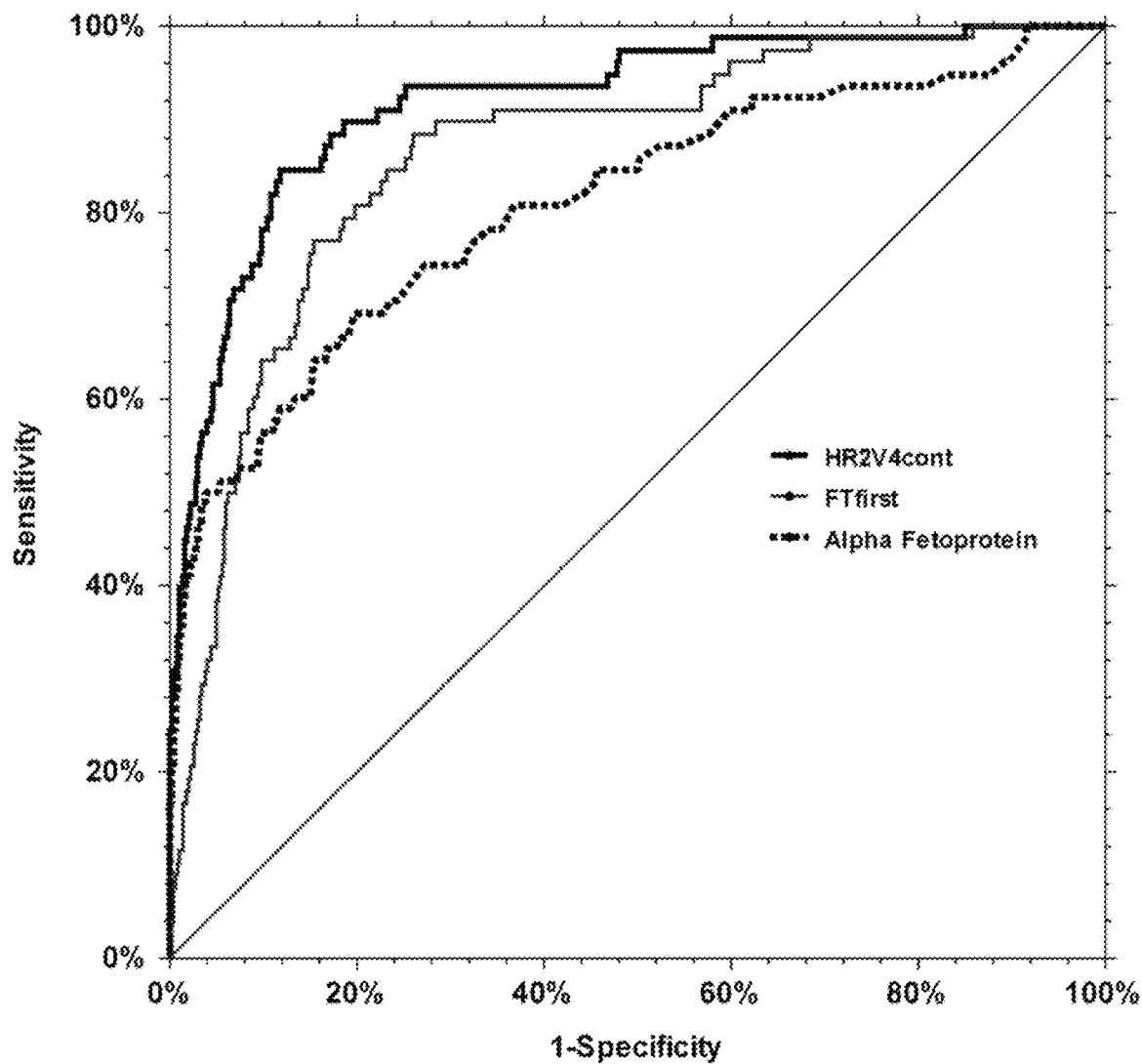
FIG. 2: Compared AUROC (Area Under Receiving Operator Curve) for detection of contemporaneous primary liver cancer from function F2-a (HR2V4cont), Fibrotest (FTfirst) and Alpha Fetoprotein.

FIG. 2 shows that a blood test using both fibrosis markers as used in Fibrotest and AFP (marker of liver cancer) is more sensitive and specific than these two tests for detecting presence of primary liver cancer (contemporaneous liver cancer), as attested by a higher AUROC. In comparison with FibroTest, AFP is more specific but much less sensitive.

FIG. 2 shows the survival without primary liver cancer over time for patients, classified in two classes according to their score with the f1-a function. One can clearly see that a score below 0.25 is indicative of a very little risk of having a primary liver cancer at 5, 10 or 15 years, while the risks increases over time (as soon as one year after the test) for patients with a score equal or above 0.25.

Figure 3:
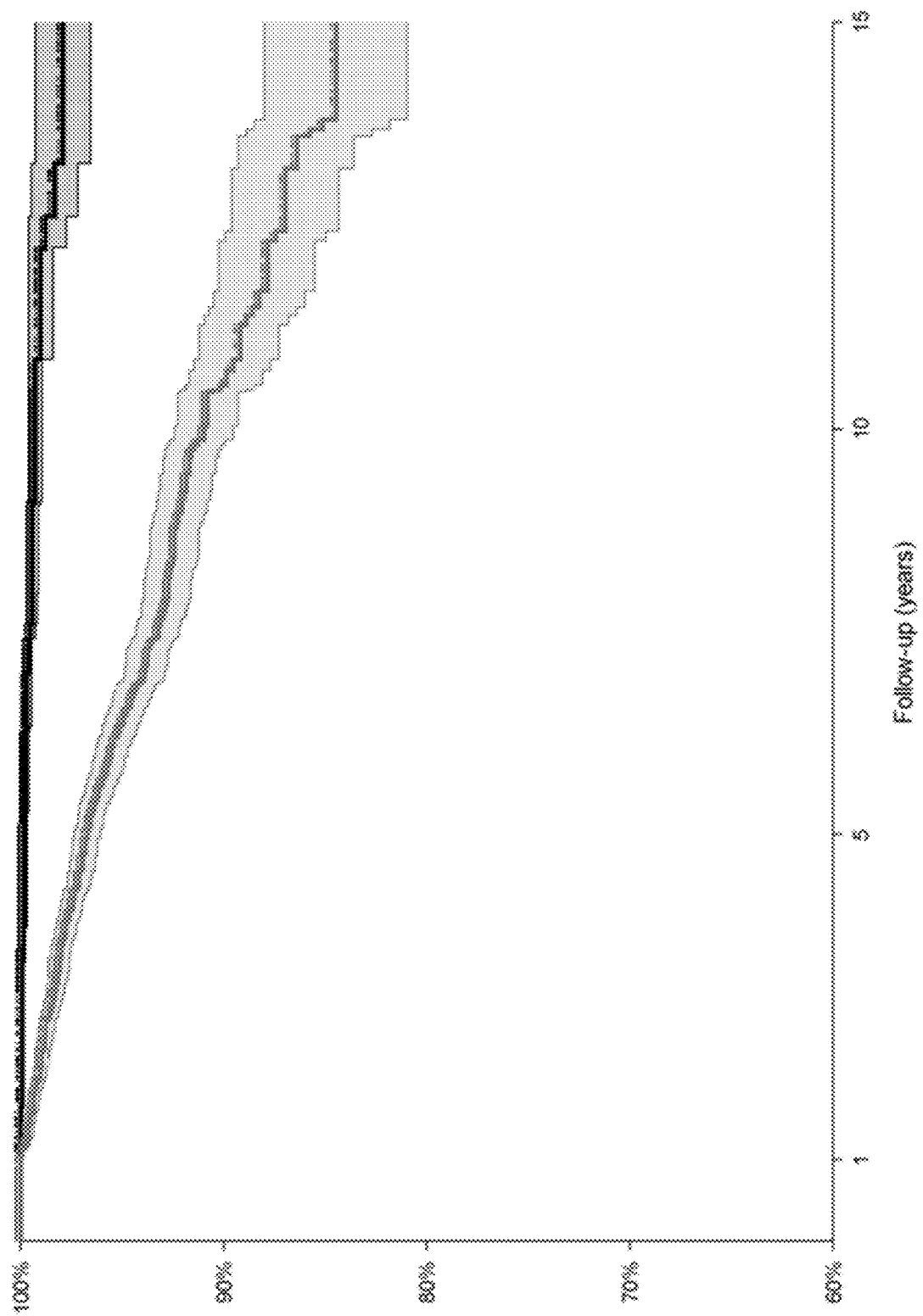
FIG. 3: Representation of the percentage of patients without cancer, overtime, depending on their classification, according to the score obtained with the f2-a function. 95% Confidence interval is represented. 0-0.25: patients with a score below 0.25; 0.25-1: patients with a score above or equal to 0.25.
Figure 4:
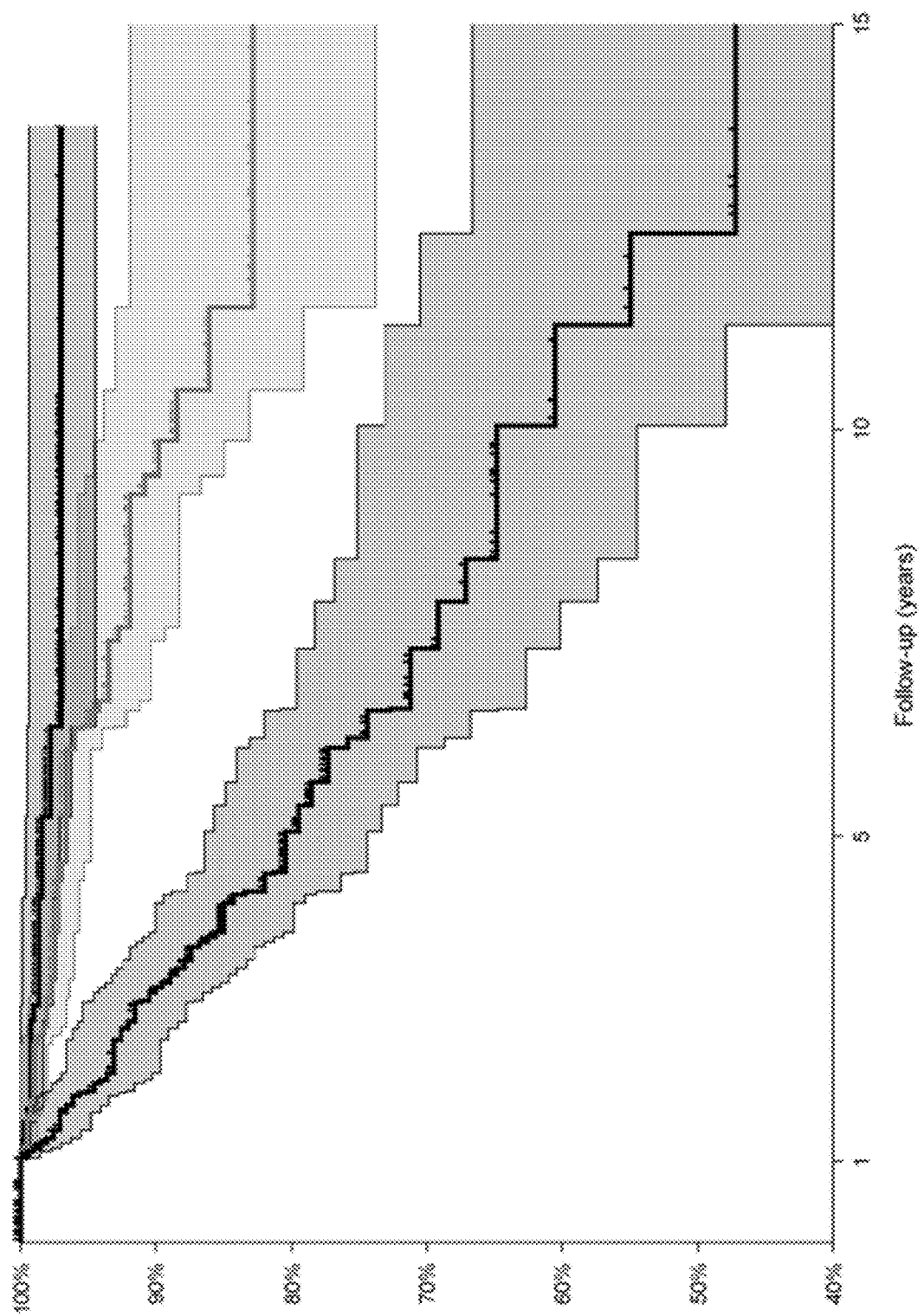
FIG. 4: Representation of the percentage of patients without cancer, overtime, depending on their classification, according to the score obtained with the f2-a function. 95% Confidence interval is indicated. HR2 25: patients with score below 0.25; HR2 2575: patients with a score above or equal to 0.25 and below 0.75; HR2 75: patients with a score above or equal to 0.75.

In FIG. 3, a test combining both fibrosis markers and a cancer marker (f2-a) has been used to classify the patients in three classes. There is a clear difference between these three classes, and a clear very increased risk of having liver cancer in the following 15 years for patients having a score higher than 0.75 at the time of the test (absolute risk of 50% at 15 years).

Figure 5:
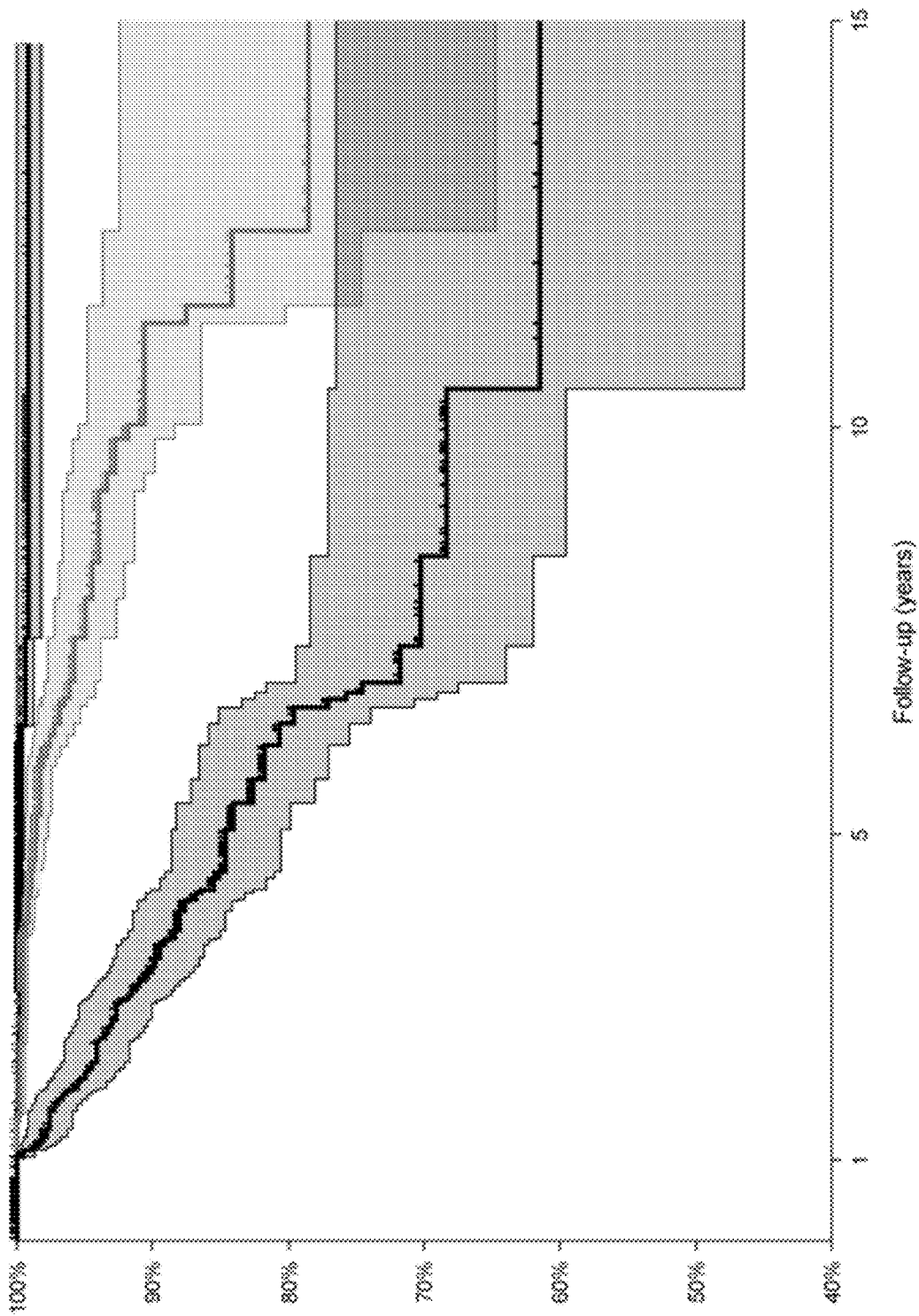
FIG. 5: Representation of the percentage of patients without cancer, overtime, depending on their classification, according to the score obtained with the f1-a function and the independent measurement of AFP level. 95% Confidence interval is indicated. AFP10 HR1 25: patients with score below 0.25 and AFP level below 10 µg/L; AFp1020 HR1 2575: patients with a score above or equal to 0.25 and below 0.75 and a AFP level between 10 and 20 µg/L; AFP20 HR1 75: patients with a score above or equal to 0.75 or AFP level above 20 µg/L.

In FIG. 5, the f1-a test and independent AFP measurement test have been used, and patients have been classified according to their results for each of these two tests. This figure shows that these two tests can be used together to obtain a risk for the patients to have the primary cancer liver over time. This can be used to identify new cancer liver markers.

Figure 6:
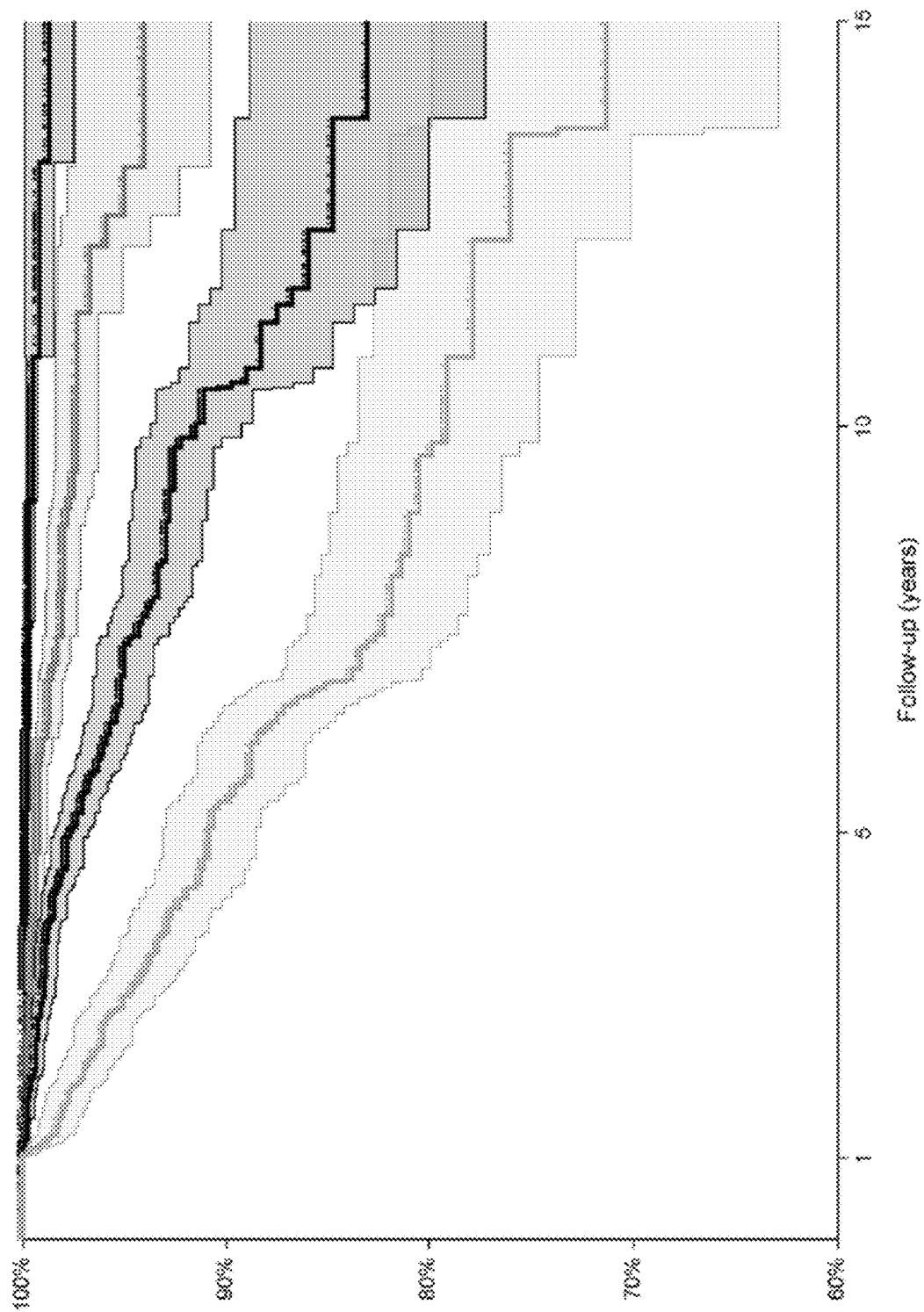
FIG. 6: Representation of the percentage of patients without cancer, overtime, depending on their classification (four classes), according to the score obtained with the f1-b function. 95% Confidence interval is indicated. 0-0.25: patients with score below 0.25; 0.25-0.5: patients with a score above or equal to 0.25 and below 0.5; 0.5-0.75: patients with a score above or equal to 0.5 and below 0.75; 0.75-1: patients with a score above or equal to 0.75.

In FIG. 6, four classes of patients with repeated tests have been determined, according to the score of f1-b. once again, it can be seen that patients with a score below 0.25 have a very little risk to have a cancer in the following 25 years.

All together, these figures show that the methods, functions, tests and scores herein disclosed are more sensitive and specific to detect contemporaneous liver cancers than existing blood tests. They are also predictive of the risk for the patient to have a primary liver cancer over the time. Furthermore, the tests are quantitative, and an increase result is indicative of an increased risk. These tests, functions and scores can be used by themselves, or together with existing liver cancer tests. They further add to the quality of these tests.

Example 3. Development of Cox Functions

A retrospective analysis in prospectively collected specimens from an ongoing cohort. To design an early sensitive high-risk test (HR1c-Test) hepatoprotective proteins (apolipoprotein A1, haptoglobin) with known risk factors (gender, age, gammaglutamyl transpeptidase), and a marker of liver fibrosis (alpha2-macroglobulin) were combined in a Cow model. Then, to increase the specificity, these components were combined with alpha fetoprotein, a direct marker of liver cancer (HR2c-Test). The primary endpoint was the prediction of liver cancer at 10 years by HR1, and a higher performance of HR2, than alfa-fetoprotein at 5 years. Results. 9,892 patients were included, 85.9% without cirrhosis, followed for a median of 5.9 years [IQR; 4.3-9.4]. Liver cancer developed in 221 patients. The time-dependent area under the ROC curve (AUROC-T) of HR1 for the prediction of cancer in the construction subset of 4,944 randomized cases was 0.874 (95% confidence interval [CI], 0.838 to 0.910), and not different in 4,948 cases in the validation subset, 0.815 (0.769-0.862; P=0.98). The AUROC-T of HR2 was higher than that of AFP alone, in the integrated data base (n=4,053), 0.870(0.834-0.905) versus 0.718(0.664-0.772; P<0.001). An algorithm combining cirrhosis-HR1-HR2 had a negative predictive value of 99.0%, and 10 cases needed to survey. Conclusions. In patients with chronic liver disease the HR1c and HR2c tests identify those with a high risk of liver cancer, including among those without cirrhosis.

Primary liver cancer (PLC), the second most frequent cause of cancer-related death, mainly develops in patients with chronic liver disease. It would be highly important to be able to discriminate among these patients, those at high risk from those at low risk of PLC. Most published PLC risk scores have included histological cirrhosis as a major component, which is a limitation due to the adverse events and the cost of biopsy. The development of non-invasive tests of fibrosis could improve the prediction of the cancer risk in large populations.

In 1997 a fibrosis blood test was constructed (FibroTest®, FibroSure in USA), and has been validated in chronic hepatitis C (CHC), and B (CHB), alcoholic liver disease (ALD), and non-alcoholic fatty liver disease (NAFLD), with similar prognostic values. Therefore, the FibroTest can replace biopsy to determine the presence or absence of cirrhosis when constructing new tests to predict at-risk candidates for surveillance.

The aim was to construct a "high-risk" individualized blood test (HR1, patent pending) to measure the 10-year risk of PLC in patients with liver disease, without or with cirrhosis. Six components were used: apoA1 and haptoglobin as markers of hepatoprotection, GGT as a marker of cytotoxicity factors, adjusted on A2M for taking into account the fibrosis severity, as well as age and gender. HR1c was constructed as a very early marker of the risk of liver cancer (HR1c), with the perspective to potentially extend the imaging surveillance so far restricted to patients with cirrhosis, to the non-cirrhotic patients with a high risk of cancer.

The second aim was to obtain an early marker of cancer (HR2c) combining the six components of HR1c with alpha-fetoprotein (AFP), for the prediction of cancer at 5 years. If HR2c had a better performance (better sensitivity) than AFP alone, it could be used in non-cirrhotic patients with elevated HR1c and in cirrhotic patients.

The third aim was to assess the efficiency of a surveillance combining HR1c and HR2c, in all patients without or with cirrhosis, in comparison with the standard surveillance (imaging and AFP) restricted to patients with cirrhosis.

For the construction and the internal validation, patients were from the "Groupe Hospitalier Pitié Salpêtrière cohort" of FIBROFRANCE, a program organized in 1997 (Clinical registry number: NCT01927133). The protocol was approved by the institutional review boards, regulatory agency and performed in accordance with principles of Good Clinical Practice. All patients provided written informed consent before entry. All authors had access to the study data and reviewed and approved the final manuscript.

Patients with a FibroTest performed before 2013, without previous PLC or liver transplantation, were selected. Follow-up and hepatitis treatments were scheduled according to updated guidelines. In patients with cirrhosis at inclusion, ultrasonography (US) examination and AFP were recommended every 6 months. The diagnosis of PLC was based on histological examination by an experienced pathologist or probabilistic noninvasive criteria. When the diagnosis of PLC was established, treatment was decided using a multidisciplinary approach. Reports of imaging techniques showing focal liver lesions were secondarily reviewed by the three senior hepatologists (TP, YN and MM) and classified according to Milan criteria.

The retention rate was defined as the number patients who came for a second fibrosis stage assessment either with FibroTest or elastography. The outcome of patients lost to follow-up was tracked by mail, call to the patient or his private physician, and by the national death registry (INSERM-CépiDC).

Statistical Analysis

Included patients were randomly divided into a construction and internal validation subset, to which model results were applied.

Construction and Validation of HR1 and HR2

The cumulative survival of patients without incident PLC was estimated with Kaplan-Meier method. Univariate and multivariate Cox proportional hazards models were used to assess the performances of components, after checking that the variables confirmed the proportional-hazard assumption using scaled Schoenfeld residuals.

The PLC risk estimate, is a predictive score based on Cox model at inclusion. Predicted PLC risks were estimated in the construction subset by the following equation: $\hat{P}=1-S_0(t)\exp(\Sigma_{i=1}^{P}\beta i x i - \Sigma_{i=1}^{P}\beta i \bar{x} i)$, where $S_0$ was inclusion PLC-free probability, ß the Cox regression coefficients, x the individual risk factors value, and $\bar{x}i$ the mean of the risk factors in construction set. The model was constructed at 10 years for HR1c, to predict very early risk of PLC, and at 5 years for HR2c to predict PLC occurrence at 5 years. The sample size of 200 events corresponded to recommendations. The performances were expressed and compared by time-dependent area under the ROC curve (AUROCt).

The first aim was to obtain a significant prognostic performance, AUROCt>0.5, for the construction subset of HR1c, without significant difference in the validation subset. The survival without PLC in patients with a low risk, defined as HR1 lower or higher than the median values, was compared to the survival of patients with high risk by the Logrank-test.

The second aim was to obtain a better performance (AUROCt) of HR2c than AFP alone in the integrated data base, combining construction and validation subsets after checking the absence of differences in their AUROCt.

Figure 7A:
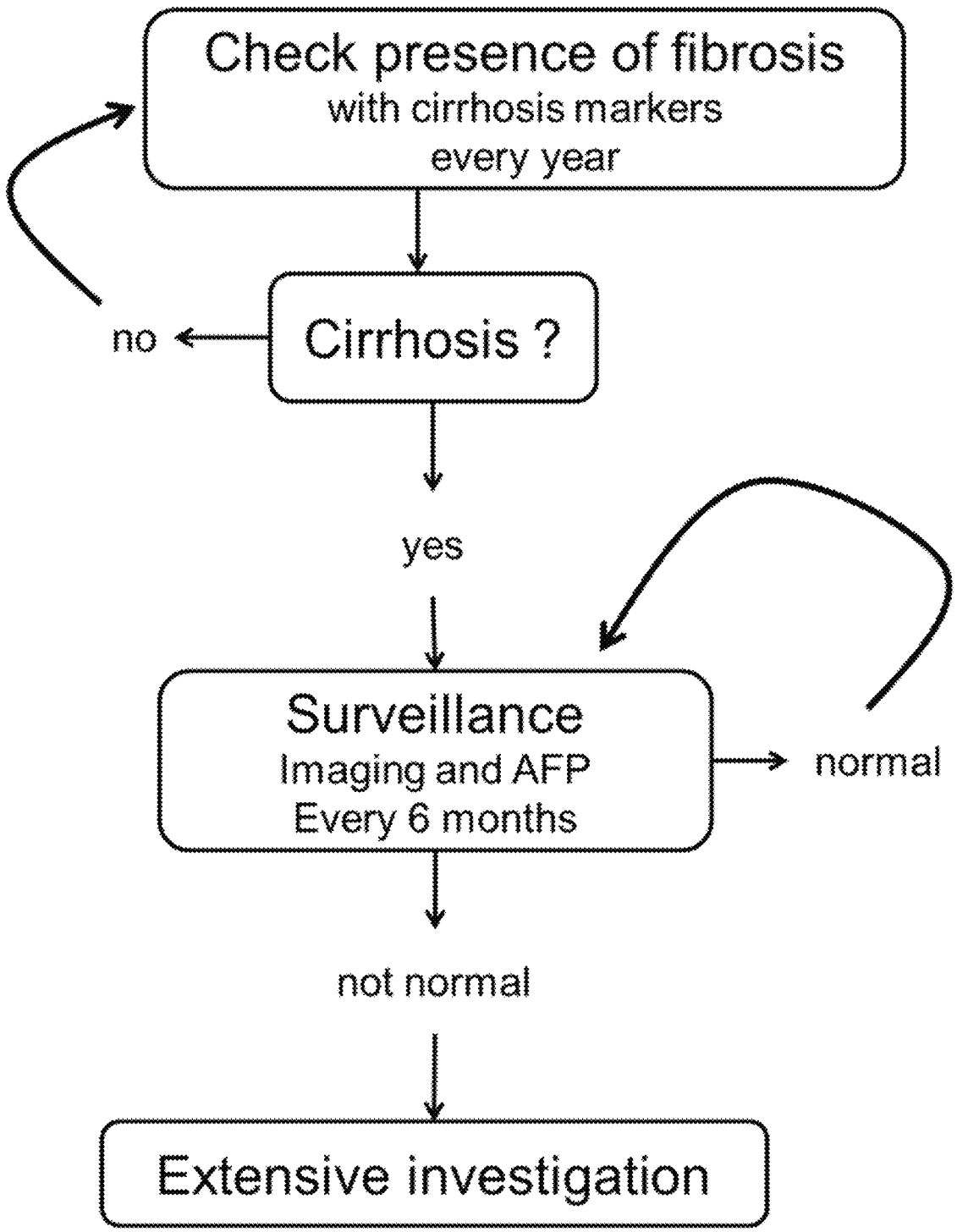
FIG. 7: Description of the follow-up and analysis of the patient state. A. Current procedure. B. proposed procedure using the functions HR1c to include further patients in the cancer surveillance (imaging and (AFP or HR2c assessment).
Figure 7B:
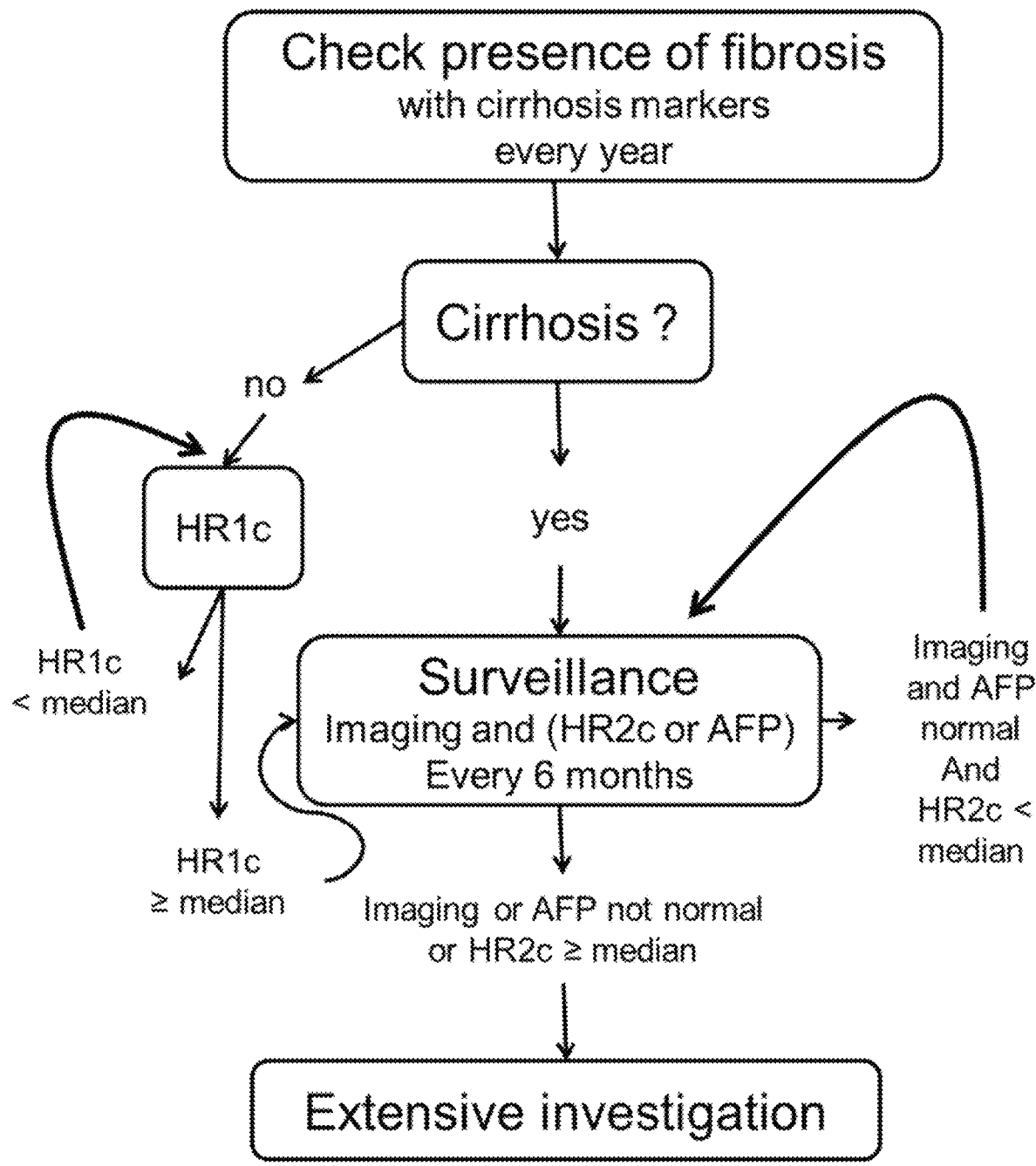

The third aim was to assess the efficiency of a surveillance combining HR1c and HR2c, in all patients without or with cirrhosis. To consider the benefits and harms, we calculated the number of subjects needed to screen (NNS) one PLC in a surveillance using the following "F4- or -HR1c-then-cancer surveillance" algorithm:

[If-cirrhosis, then surveillance(imaging+(either HR2c or dosage of AFP)); if-no-cirrhosis and HR1c-high-(≥median)-then-HR2c, and if HR2c-high-(≥median), then surveillance (imaging+HR2c or dosage of AFP)] This algorithm is represented in FIG. 7.B.

In other words, patient with cirrhosis (as determined, for example by Fibrotest® or another method such as Fibroscan®) shall have cancer surveillance (imaging+HR2c or dosage of AFP).

For patients without cirrhosis, HR1c will be performed. If the value of HR1c is higher than the median, then the patient shall have cancer surveillance (imaging+HR2c or dosage of AFP).

In fact the HR1c formula makes it possible to include further patients (some patients without cirrhosis with HR1c value≥median) in the cancer surveillance scheme.

The current cancer surveillance scheme consists in imaging and measure of AFP level every 6 months, unless one of the values is not normal, which would then require extensive investigation.

This current scheme may still be performed for patients with a PLC risk (patients with cirrhosis and patients with HR1c value≥median).

However, it is advantageous to perform a HR2c test in addition with imaging, rather than the sole dosage of AFP. Indeed, the HR2c test combines the values of HR1c+the value of AFP and has proven to be more effective than AFP alone.

Consequently, it is proposed to change the cancer surveillance scheme, for patients at risk, to imaging and calculation of HR2c every 6 months, unless imaging is not normal or HR2c is higher than the mean, which would then require extensive investigation.

In summary, the formulas herein disclosed make it possible to 1) increase the number of people that are at risk for Primary Liver Cancer surveillance (and thus increase sensitivity), through the HR1c formula, and 2) to improve the quality of cancer surveillance through the HR2c formula.

It is also to be noted that other formulas described or taught herein can be used in place of HR1c and HR2c. Formulas for the inclusion of patients in the "at risk" population are the ones that do not contain a liver cancer marker (such as the F1, F1-a, F1-b, or C1 functions disclosed above), whereas the formulas for cancer surveillance contain a liver cancer marker such as AFP (and are the F2, C2 and C3 functions and other functions such as these that can be developed using the teachings of the present specification).

The comparator was the standard surveillance by (imaging+AFP) restricted to patients with cirrhosis. NNS restricted to patients 50 years of age or older, a well-known PLC risk-factor were assessed to improve the efficiency.

To assess calibration, the observed risk of developing PLC during the study period was plotted against predicted risk by Hare approach Sensitivity Analyses AUROCt of HR1c and HR2c were assessed and compared, in the integrated database, according to the absence or presence of cirrhosis at inclusion, as defined by the standard FibroTest cutoff of 0.74. To prevent any influence of colinearity from the stratification by FibroTest, which shares components with HR1c and HR2c, three other definitions of cirrhosis were used; elasticity>12.5 k-Pascal alone, biopsy alone or at least one of these two methods.

The impact of patient characteristics was assessed, which can artificially change the AUROCs by a spectrum effect, in patients with inclusion PLC, and in patients who had repeated HR1c-HR2c measurements. One analysis (Cox model) assessed which characteristics were independently associated with incident PLC, and another one (logistic regression) those associated with cirrhosis. In order to homogenize the criteria of response (chronic viral suppression, diabetic treatment, weight or alcohol consumption) appropriate for the different liver diseases during the follow-up, ALT transaminase was used as an indirect markers of necro-inflammatory activity, without risk of colinearity as ALT is not a FibroTest component. A significant improvement of HR1c was defined as a decrease of at least one quartile between the inclusion and the repeated HR1c. Uni and multivariate analysis of factors associated with the improvement were assessed using logistic regression.

After checking the discriminative performances of the interquartile range cutoffs of HR1,c these cutoffs in 3 external populations were applied to estimate the prevalence of 4 levels of PLC risk, IQR-1=very low, IQR-2=low, IQR-3=moderate, IQR-4=elevated. One population included 7,554 healthy volunteers, one included 133,055 American high-risk patients with NAFLD, and one included 728,051 American high-risk patients with CHC.

All statistical analyses were performed using NCSS-12.0 and R softwares, including timeROC library.

Results

Among 10,481 consecutively enrolled patients, 453 were not included. The cohort retention rate was 62.8% (6,581 out of 10,481). A total of 10,028 patients were included and randomly assigned to the construction (n=5,014) or validation (n=5,014) subsets. Patient characteristics were similar between the randomized subsets. The most frequent unique causes of chronic liver disease were CHC (34.3%), and CHB (20.5%). During follow-up viral suppression was achieved in almost all cases of CHB (97.0%), and 46.9% of CHC. In the population (n=9,892) without contemporaneous PLC, after a median follow-up of 5.9 years [IQR; 4.3-9.4], PLC was diagnosed in 221 patients. Overall, 138 (74.3%) detected PLC were potentially resectable and 166 (75.5%) patients fulfilled Milan criteria for transplantation. There were no significant differences in PLC characteristics between the construction and validation subsets. The population of HR2c (n=4,053) had more cirrhosis and more PLC than for HR1c due to the surveillance of cirrhosis by AFP.

Construction and Validation of HR1c and HR2c

The proportional hazards assumption for the six components was validated, and calibration plot was acceptable for the 10 years' follow-up.

HR2c corresponds to C3=0.68030×Log AFP (µg/L)−1.13208×ApoA1 (g/L)−0.82013×Log Hapto (g/L)+1.20152 Log GGT (IU/L)+1.39771×Log A2m (g/L)+0.07582×Age (years)+0.31238×Sex (0 for women, 1 for men).

HR1c corresponds to C1-b=0.67930×ApoA1 (g/L)−1.05404×Log Hapto (g/L)+1.46545×Log GGT (IU/L)+2.65740×Log A2m (g/L)+0.06346×Age (years)+0.97350×Sex (0 for women, 1 for men).

First Aim

The AUROCt of HR1c was 0.874 (0.838-0.910) in the construction and 0.815 (0.769-0.862) in the validation subset, a non-significant difference (P=0.06), the primary endpoint. In the construction subset only ten patients out of 2,528 with a HR1c<median(0.039) had PLC, representing 10-year survival without PLC 99.2% (98.7-99.7), vs. 98 out of 2,420, 93.1% (91.7-94.7; P<0.001) in patients with HR1c≥median, with similar results in validation subset, 7 out of 2,472 99.6% (99.3-100.0) vs. 106 out of 2,472, 93.0% (91.4-94.6; P<0.001). This amounts to a very interesting Negative Predictive Value VPN).

Second Aim

The HR2c AUROCt was higher than that of AFP alone, in the integrated data base (n=4,053) 0.870(0.834-0.905) vs 0.718(0.664-0.772; P<0.001). The prediction of cancer with HR2c was 0.902 (0.860-0.945) in the construction and not different in the validation subset, 0.828(0.771-0.886; P=0.98). In the construction subset only 2 patients out of 1,008 with HR2c<0.026 (median) had PLC, representing 99.8% (99.5-100) 5-year survival without PLC, vs. 52 out of 1007 i.e. 93.9% (92.3-95.6; P<0.001) in patients with a high HR2, with similar results in the validation subset. Here again, the VPN is very high HR1c and HR2c, had significantly higher AUROCs than those of each component alone, which all had significant risk ratio for PLC.

Third Aim.

Applying retrospectively the HR1c and HR2c tests in the 4,053 cases with both tests, permitted to demonstrate the possible efficiency of surveillance of all patients including non-cirrhotic. The algorithm ("F4orHR1thenHR2") reached a NSS=10 (1930/183) and a negative predictive value=99.2%(2,105/2,123 vs. 26 (755/127) and 97.8%(3,224/3,298) for the standard surveillance. In patients who were 50-years of age or older, the results were always in favor of the algorithm ("F4orHR1thenHR2"), with NNS=10 and negative predictive value=99.5% vs NNS=5, but much lower negative predictive value (96.5%) for the standard surveillance.

This determines a new decision tree and procedure for the physician (FIG. 7.B)

(1) determine whether a patient has cirrhosis (2a) if the patient has cirrhosis, make surveillance (imaging and either dosage of AFP or dosage of HR2c or of a function as developed herein containing biochemical markers as herein disclosed and at least a marker for cancer)

(2b) if the patient has not cirrhosis, perform HR1c (or a function as developed herein containing biochemical markers as herein disclosed but no marker for cancer)

(3a) if the value of HR1c is below the median, do not perform other specific surveillance, and follow and/or treat the patient on a regular basis for his liver disease (3b) if the value of HR1c is higher or equal to the median, then perform surveillance as disclosed above (4a) if the imaging data is normal and either the AFP value (if measured) is normal, or the value of HR2c (if measured) is below the median, do not perform other specific surveillance, and follow and/or treat the patient on a regular basis for his liver disease with new surveillance about 6 months later, (4b) if at least one of the following occurs i) the imaging is not normal, or ii) the AFP value (if measured) is not normal, or iii) the value of HR2c is higher or equal to the median, then make extensive investigation for HCC or CC diagnosis and treatment.

Sensitivity Analyses According to the Absence or Presence of Cirrhosis

AUROCt of HR1c was higher in patients without, than in those with cirrhosis in the randomized subsets, in the integrated data-base and in cases with simultaneous HR1c, HR2c and AFP. Among 4,990 non-cirrhotic cases with low HR1, 17 PLC occurred (99.4%; 99.1-99.7), versus 67 (96.6%; 95.7-97.6) with high HR1 out of 3,507 at 10 years ($P<0.001$).

In patients with cirrhosis, the AUROCt of HR2c was 0.727 (0.664-0.789) versus 0.642 (0.575-0.709; P=0.06) for AFP, and in patients without cirrhosis 0.773 (0.678-0.869) versus 0.680 (0.569-0.790; P=0.21) respectively. Among 10 cirrhotic cases with low HR1c, 0 PLC occurred at 15 years, a 100% (C1 not estimated) 10-year survival without PLC, vs 137 out of 1385 (84.7%; 81.1-87.0); P=0.001) in patients with high HR2c.

Sensitivity Analyses According to the Cirrhosis Definitions

The presence of cirrhosis was obtained by elastography, biopsy, and one of these two methods in 2,897, 895 and 3,552 cases, in cases with HR1c, and in 1858, 462 and 2160 cases, with HR2c, respectively. Results were similar to those observed using the FibroTest for cirrhosis definition, with AUROCt of HR1c range=0.802-0.825, and HR2c range=0.780-0.850.

Sensitivity Analyses According to the Main Characteristics of Patients

Although HIV was associated with cirrhosis, it was not predictive of PLC, suggesting a benefit of HIV treatment. Although it was not associated with cirrhosis, the presence of diabetes was predictive of PLC, suggesting a mechanism independent of the progression of fibrosis.

Confounding Covariates and Interpretation of AUROCs

As expected the HR1c AUROCt were higher (significantly or not) among patients without cirrhosis than among patients with cirrhosis, for almost all characteristics, except in patients with HIV infection. This result cannot be clearly interpreted due to the small number of liver cancer, five in non-cirrhosis HIV.

Other Sensitivity Analyses

The AUROCt of HR1c and HR2c were not different according to the different liver diseases and ethnicities, as well as the exclusion of 8 cases with cholangiocarcinoma (data not shown).

For the diagnostic of contemporaneous PLC (121/4,047), the AUROC of HR2c (0.905; 0.875-0.928) was higher ($P<0.001$) than that of AFP (0.796; 0.741-0.840) due to the increase in sensitivity.

Repeated measurements of HR1c were performed in 3,931 patients, 3.6 years (3.6-7.0) after inclusion. An improvement of at least one quartile of HR1c was observed in 245 (6.2%) cases, and was highly associated in uni or multivariate analyses to the improvement of necrosis and inflammation assessed by ALT (odds ratio=19.8; 13.4-29.3; $p<0.001$) after adjustment with inclusion characteristics. Among the 245 cases with improvement of HR1c, 3 PLC occurred (1.2%) vs 140 (3.6%) among the 3,646 patients without HR1c improvement (Fisher-exact test p=0.03).

A subset of 1,856 patients had repeated measurements for both HR1c and HR2c 3.99 years (IQR 1.86-6.62) after inclusion, and the AUROCs remained both significant for the prediction of cancer (130/1856; 7% incidence), 0.821 (0.730-0.834) and 0.837(0.782-0.891) respectively, higher than repeated AFP (0.706; 0.637-0.775).

Discriminative Value of HR1 Interquartile Cutoffs.

After pooling the construction and validation cohorts, a possible choice for patients with chronic liver disease could the IQR-2 (the median cutoff), with a specificity of 0.892 and a sensitivity of 0.333. With a prevalence of PLC of 1%, the negative predictive value was 0.993 (95% CI 0.990-0.994) raising to 0.999 if the prevalence of PLC was 1/1000.

Levels of PLC Risk in External Populations

The presumed survival without PLC in external applications for each quartile of HR1c was assessed according to age and gender. According to the context of use, age and gender, the prevalence of high risk at 10 years (HR1c=IQR-4) varied from 0%(0-0.004)(0/895) in healthy women younger than 50 years, to 56.4%(55.8-56.9; 21,542/38,196) in men aged 50 years or older in NAFLD, and 73.5%(73.3-73.6; 227,964/310,305) in CHC.

DISCUSSION

In the present study two multi-analyte blood tests were constructed and internally validated, HR1c, which permitted to identify high risk non-cirrhotic patients at 10 years, and HR2c which had higher performance than AFP for the prediction of PLC occurrence at 5 years, both in patients without and with cirrhosis. The results strongly suggest that assessing HR1c in non-cirrhotic patients, and HR2c both in patients with cirrhosis or in patients without cirrhosis but with high HR1c, should improve the efficiency of the standard surveillance with ultrasonography and AFP, restricted to patients with cirrhosis. This simple algorithm had a high sensitivity and a high negative predictive value, without increasing significantly the number of patients to screen (n=10) for the detection one cancer, in patient 50 years of age or older.

Comments for this Retrospective Analysis of a Prospective Cohort are as Follows

The first strength was to demonstrate the performance of these tests in patients without cirrhosis, who represented 86% of the cohort. Thus far, most patients without cirrhosis have been investigated in CHB cohorts. Only one study used elastography, which was found to have predictive value, but no multi-analyte test was constructed. Only one study has constructed a test in patients with CHC without cirrhosis at biopsy, but they did not use any validated marker of fibrosis.

Also, the core analysis only included incident PLC detected after the first year of follow-up. Thus, incident PLC were at early stage with 80% of possible resection.

Moreover, although our population was selected from a tertiary center, there was a broad spectrum of patient characteristics, including all stages of fibrosis (48% without fibrosis), different causes of liver disease, ethnicities, and comorbidities. Performance was similar in all these subsets. It is acknowledged that the cohort was designed 20 years ago to validate the performance of non-invasive fibrosis biomarkers, and had a biological surveillance close to the cirrhotic subjects even if twice less AFP were performed. Because of this particular context of use, and according to the small number of incident PLC, external validation must be performed.

Nonetheless, the prospective follow-up was long enough to obtain a sufficient number of events and to validated repeated tests performances in 1,856 patients(. In another study, the estimated 10-year incidence of PLC was 4.8% in HBV Asian male carriers without metabolic factors. When our subset of Asian males without type-2 diabetes was analyzed, the cancer 10-year incidence (7/227) was similar, i.e. 4.2% (0.8-6.5).

Fifth, factors linked to PLC were combined by different potential mechanisms. Whereas GGT had similar risk ratios in patients with and without cirrhosis, ApoA1 and haptoglobin potential markers of hepatoprotection, had a higher risk ratio for predicting PLC in patients without cirrhosis than in those with cirrhosis.

Thus, HR1c was a sensitive test that identified high risk cases with no specific marker of PLC and independently of the presence of cirrhosis. Furthermore, HR2c combining the HR1c components with AFP, the standard specific PLC marker, had a higher specificity without decreasing the sensitivity compared to AFP alone.

This strategy could easily be further improved with other available specific PLC markers. Recently, a study combined proteins and genetic biomarkers (CancerSEEK) to increase sensitivity without decreasing specificity for the detection of contemporaneous solid tumors. This test had an AUROC of 0.910 (0.900-0.920). The AUROC for HR2c were similar for the diagnosis of contemporaneous PLC, i.e. 0.917(0.887-0.939). Appropriate comparisons require direct comparisons in the same patients, but the analysis validated HR2c for incident PLC using patients with liver disease as controls rather than healthy controls, who may have artificially increased the performance of CancerSeek. Two of the CancerSEEK components, the tissue inhibitor of metalloproteinases-1 and the hepatocyte growth factor, are connected to the two proteins used in HR1c, A2M and haptoglobin.

Finally, HR1c and HR2c combined simple, available and affordable components, in which the risks of false positive and negative are well known. When HR1c was applied in different contexts of use, the high risk of PLC at 10 years varied from 0% in healthy women younger than 50 years to 74% in male with CHC and of 50 years of age or older. Among patients with chronic liver diseases, the high negative predictive value of HR1c should permit to identify the patients without cirrhosis who will benefit of the same surveillance than patients with cirrhosis.

The construction of HR1c was focused for patients without cirrhosis, according to the possible but not established increase of PLC occurrence in CHB carriers and in NAFLD patients without cirrhosis, including obese patients and type-2 diabetics. There was an unmet need to validate a new test in patients without cirrhosis, but HR1c has little or no clinical interest in patients with cirrhosis, as cirrhosis is already known to be a main risk factor of PLC. HR2c has a clinical utility both in patients without cirrhosis and high HR1c, and also in patients with cirrhosis.

Also, it is acknowledged other potential components that could provide additional predictive value for a single liver disease such as HBV or HCV markers, and family history of HCC were not included.

In addition, the predictive value of evolving risk factors during follow-up was not analyzed, such as alcohol intake or diabetes. At least the performances of the tests persisted among the large subset with repeated samples. the predictive value of steatosis, overweight, tobacco, coffee, chocolate or *cannabis* consumption, physical exercise or long-term drug use, all of which could be associated with fibrosis or the risk of PLC, were also not analyzed. However, GGT was highly associated with the risk of PLC, probably due to its association with cytotoxicity factors such as alcohol and metabolic factors. Indeed, the presence of type-2-diabetes was predictive of PLC, although it was not associated with cirrhosis at inclusion, suggesting a mechanism independent of the progression of fibrosis. The association between nonalcoholic fatty liver disease and risk for hepatocellular cancer, based on systematic review, is not validated, but highly suspected in patients without cirrhosis.

Several known or unknown factors can be associated with the risk of PLC during a 10 years' follow-up. Here the aim for HR1c was to construct a very early sensitive marker of PLC risk, in the pragmatic context of use, assuming the possible variability due to these factors. In order to homogenize a criteria of response appropriate for the different liver diseases (viral suppression, diabetic treatment, weight or alcohol consumption) during the follow-up, ALT transaminase was used as a marker of necro-inflammatory activity. Results showed a very high association between the improvement of HR1c and those of ALT, as well as CHC as a cause of liver disease, in line with the beneficial effect of chronic viral suppression in these patients. In this large cohort, the proportional hazard assumption was validated and no significant covariates were identified, with only a small age effect which should be checked in external validation.

When considering a screening test, once must consider the benefits and harms, including the false positive impact. A cost-efficiency analysis was not performed, but the simple analysis of the number needed to screen and the negative predictive value suggested that the surveillance of patients without cirrhosis by the algorithm combining HR1c and HR2c could be compared to the standard including only cirrhosis.

Another limitation could be that surveillance is cost effective when PLC annual incidence is above 1%. Here, in the population with HR1c and HR2c, the years incidence was 13% (95% CI 10-16%), that is 0.9% after exclusion of the first year where PLC were not included and 1.1% if restricted to patients older that 50 years.

Diagnosis of PLC at early stage is susceptible to biases such as lead-time bias (apparent improvement of survival because of an anticipated diagnosis, mainly occurring in follow-up shorter than 5 years) and length time bias (over-representation of slower-growing tumors). Here the risk was minimal, as HR1c was not designed to diagnose a small cancer, but to identify risk profiles 10 years before the occurrence of cancer, including non-cirrhotic cases. For HR2c, the endpoint was at 5 years, but all PLC occurring the first year were not included, and same performances were observed at 10 or 15 years. Moreover, the comparator AFP shared the same risk of bias than HR2c.

It is acknowledged also that only 41% of our cases underwent AFP measurements, now more recommended together with ultrasonography. Other combinations should also be tested with imaging and forthcoming new direct PLC makers. The multi-analyte test HR2c, used the HR1c components combined with AFP alone as a PLC specific marker, but we did not combine second generation PLC biomarkers, which could further improve the quality of HR2c.

In conclusion, in patients with chronic liver disease two tests with significant performances were constructed, HR1c for the early stratification of cancer risk in non-cirrhotic patients and HR2c for increasing the sensitivity of AFP alone. External validation should permit to extend imaging surveillance after the age of 50, to patients without cirrhosis with high HR1c, and to confirm the increased performance of HR2c versus AFP alone, in patients with cirrhosis and in patients without cirrhosis with high HR1c.

The invention claimed is:

1. A method for treating a patient with liver disease at risk for primary liver cancer comprising:
   (A) identifying the patient with liver disease who is at risk for primary liver cancer by:
      (i) ascertaining age in years of a patient with liver disease;
      (ii) assigning a number based on gender to the patient, wherein 0 is assigned to a female and 1 is assigned to a male;
      (iii) obtaining measurements of a2-macroglobulin (A2M), gammaglutamyl transpeptidase (GGT), haptoglobin (Hapto), apolipoprotein A-1 (apoA1), and optionally alpha-fetoprotein (AFP) in blood, serum, or plasma from the patient;
      (iv) combining the age in years, the number based on gender, and the measurements to obtain an end-value according to a function selected from:
         (a) $a0 + a1 \times \text{Log (A2M, g/l)} + a2 \times \text{Age (years)} + a3 \times \text{ApoA1 (g/l)} + a4 \times \text{Gender (0 for women, 1 for men)} + a5 \times \text{Log (GGT, IU/l)} + a6 \times \text{Log (Hapto, g/l)}$, wherein $-6 \leq a0 \leq -3.4$, $2.4 \leq a1 \leq 4.6$, $0.02 \leq a2 \leq 0.07$, $-2.6 \leq a3 \leq -0.8$, $-1.5 \leq a4 \leq -0.5$, $0.9 \leq a5 \leq 1.9$, and $-1.5 \leq a6 \leq -0.5$;

(b) $a0 + a1 \times \text{Log (A2M, g/l)} + a2 \times \text{Age (years)} + a3 \times \text{ApoA1 (g/l)} + a4 \times \text{Gender (0 for female, 1 for male)} + a5 \times \text{Log (GGT, IU/l)} + a6 \times \text{Log (Hapto, g/l)} + a7 \times \text{Log (AFP, µg/L)}$, wherein $-7 \leq a0 \leq -5.5$, $2.2 \leq a1 \leq 3.2$, $0.02 \leq a2 \leq 0.06$, $-1.65 \leq a3 \leq -1.25$, $-0.3 \leq a4 \leq -0.22$, $1.25 \leq a5 \leq 1.85$, $-0.75 \leq a6 \leq -0.55$, and $1.3 \leq a7 \leq 1.9$;

(c) $b1 \times \text{ApoA1 (g/L)} - b2 \times \text{LogHapto (g/L)} + b3 \times \text{Log GGT (IU/L)} + b4 \times \text{Log A2m (g/L)} + b5 \times \text{Age (years)} + b6 \times \text{Sex (0 for female, 1 for male)}$, wherein $0.6 \leq b1 \leq 0.8$, $1.0 \leq b2 \leq 1.1$, $1.4 \leq b3 \leq 1.5$, $2.6 \leq b4 \leq 2.7$, $0.05 \leq b5 \leq 0.07$, and $0.8 \leq b6 \leq 1.1$;

(d) $c1 \times \text{Log AFP (µg/L)} - c2 \times \text{ApoA1 (g/L)} - c3 \times \text{LogHapto (g/L)} + c4 \text{ Log GGT (IU/L)} + c5 \times \text{Log A2m (g/L)} + c6 \times \text{Age (years)} + c7 \times \text{Sex (0 for female, 1 for male)}$, wherein $0.8 \leq c1 \leq 1.0$, $0.7 \leq c2 \leq 0.9$, $0.5 \leq c3 \leq 0.7$, $1.1 \leq c4 \leq 1.3$, $1.4 \leq c5 \leq 1.5$, $0.06 \leq c6 \leq 0.08$, and $0.4 \leq c7 \leq 0.6$; and (e) $d1 \times \text{Log AFP (µg/L)} - d2 \times \text{ApoA1 (g/L)} - d3 \times \text{LogHapto (g/L)} + d4 \text{ Log GGT (IU/L)} + d5 \times \text{Log A2m (g/L)} + d6 \times \text{Age (years)} + d7 \times \text{Sex (0 for female, 1 for male)}$, wherein $0.6 \leq d1 \leq 0.8$, $1.0 \leq d2 \leq 1.2$, $0.7 \leq d3 \leq 0.9$, $1.1 \leq d4 \leq 1.3$, $1.3 \leq d5 \leq 1.5$, $0.06 \leq d6 \leq 0.09$, and $0.2 \leq d7 \leq 0.4$;

(v) comparing the end-value to a predetermined value and identifying the patient with primary liver disease who is at risk for liver cancer based on deviation between the end-value and the predetermined value; and (B) treating the patient with liver disease who is at risk for primary liver cancer with intra-arterial chemo-embolization, an antitumor drug, or a combination thereof.

2. The method of claim 1, wherein the function is selected from:
- (a) (i) −4.819+3.673×Log A2M (g/L)+0.053×Age (years)−1.983×ApoA1 (g/L)−1.122×Sex (0 for female, 1 for male)+1.603×Log GGT (IU/L)−0.834×LogHapto (g/L),
- (a) (ii) −4.982+3.713×Log A2m (g/L)+0.0473×Age (years)−1.133×ApoA1 (g/L)−0.791×Sex (0 for female, 1 for male)+1.343×Log GGT (IU/L)−1.062×LogHapto (g/L),
- (b) (i) −6.214+2.713 Log A2m (g/L)+0.0447×Age (years)−1.451×ApoA1 (g/L)−0.260×Sex (0 for female, 1 for male)+1.557×Log GGT (IU/L)−0.633×LogHapto (g/L)+1.662×Log AFP (µg/L),
- (c) (i) 0.67930×ApoA1 (g/L)−1.02404×LogHapto (g/L)+1.46545×Log GGT (IU/L)+2.65740×Log A2m (g/L)+0.06346×Age (years)+0.97350×Sex (0 for female, 1 for male),
- (c) (ii) 0.67930×ApoA1 (g/L)−1.05404×LogHapto (g/L)+1.46545×Log GGT (IU/L)+2.65740×Log A2m (g/L)+0.06346×Age (years)+0.97350×Sex (0 for female, 1 for male),
- (d) (i) 0.88166×Log AFP (µg/L)−0.82480×ApoA1 (g/L)−0.62809×LogHapto (g/L)+1.20973 Log GGT (IU/L)+1.42462×Log A2m (g/L)+0.07235×Age (years)+0.53213×Sex (0 for female, 1 for male), and
- (e) (i) 0.68030×Log AFP (µg/L)−1.13208×ApoA1 (g/L)−0.82013×LogHapto (g/L)+1.20152 Log GGT (IU/L)+1.39771×Log A2m (g/L)+0.07582×Age (years)+0.31238×Sex (0 for female, 1 for male).

3. The method of claim 1, wherein the predetermined value is 0.25 and the patient is at risk of developing a primary liver cancer if the end result is higher than or equal to 0.25.

4. The method of claim 1, wherein the liver disease is a chronic liver disease.

5. The method of claim 4, wherein the chronic liver disease is selected from infection with hepatitis B virus, infection with hepatitis C virus, Non-Alcoholic Fatty Liver disease (NAFLD), Alcoholic Liver Disease (ALD), or Non-Alcohol Steatohepatitis (NASH).

\* \* \* \* \*